US012661277B2

(12) United States Patent
Jeong et al.

(10) Patent No.: US 12,661,277 B2
(45) Date of Patent: Jun. 23, 2026

(54) MULTI-LAYER ABSORBENT CORES AND METHODS OF MANUFACTURE

(71) Applicant: Kimberly-Clark Worldwide, Inc., Neenah, WI (US)

(72) Inventors: YunSeok Jeong, Seoul (KR); WonYoung Lee, Gyeonggi-do (KR); MinHee Lee, Anseong-si (KR); SukHee Jung, Sejong-si (KR)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 341 days.

(21) Appl. No.: 18/547,894

(22) PCT Filed: Mar. 30, 2021

(86) PCT No.: PCT/US2021/024823
§ 371 (c)(1),
(2) Date: Aug. 25, 2023

(87) PCT Pub. No.: WO2022/211787
PCT Pub. Date: Oct. 6, 2022

(65) Prior Publication Data
US 2024/0139043 A1      May 2, 2024

(51) Int. Cl.
*A61F 13/15*          (2006.01)
*A61F 13/534*         (2006.01)
(Continued)

(52) U.S. Cl.
CPC .. *A61F 13/53418* (2013.01); *A61F 13/15577* (2013.01); *A61F 13/536* (2013.01); (Continued)

(58) Field of Classification Search
CPC .......... A61F 13/53418; A61F 13/15577; A61F 13/536; A61F 13/537; A61F 13/539; (Continued)

(56) References Cited

U.S. PATENT DOCUMENTS 5,019,069 A      5/1991  Klemp
5,211,641 A      5/1993  Roos et al.
          (Continued)

FOREIGN PATENT DOCUMENTS

CA          2248633 A1      3/2000
CN          1158558 A       9/1997
          (Continued)

OTHER PUBLICATIONS

Mölnlycke, "Mölnlycke Health Care", Nov. 29, 2017, http://www.molnlycke.us/see-the-proof/patented-design/5-unique-layers/.
          (Continued)

*Primary Examiner* — Jacqueline F Stephens
(74) *Attorney, Agent, or Firm* — KIMBERLY-CLARK WORLDWIDE, INC.

(57)          ABSTRACT

Absorbent bodies and methods of forming absorbent bodies are disclosed. In one embodiment, an absorbent garment comprises a bodyside liner; an outer cover; an absorbent comprising: a top facing material layer, a bottom facing material layer, a lofty nonwoven reinforcing material disposed between the top facing material layer and the bottom facing material layer, absorbent material comprising superabsorbent material disposed between the top facing material layer and the bottom facing material layer and within the reinforcing material; and an acquisition material disposed between the absorbent body and the bodyside liner, wherein a first side of the absorbent body and a second side of the absorbent body are folded onto a central portion forming a folded absorbent body with first and second folded portions with a channel region disposed between the first and second folded portions, and wherein the acquisition material spans across the channel region.

19 Claims, 15 Drawing Sheets

(51) Int. Cl.

| | |
|---|---|
| *A61F 13/536* | (2006.01) |
| *A61F 13/537* | (2006.01) |
| *A61F 13/539* | (2006.01) |
| *A61F 13/53* | (2006.01) |

(52) U.S. Cl.
CPC .......... *A61F 13/537* (2013.01); *A61F 13/539* (2013.01); *A61F 2013/15869* (2013.01); *A61F 2013/15878* (2013.01); *A61F 2013/530481* (2013.01); *A61F 2013/53463* (2013.01); *A61F 2013/53908* (2013.01)

(58) Field of Classification Search
CPC .. A61F 2013/15869; A61F 2013/15878; A61F 2013/530481; A61F 2013/53463; A61F 2013/53908
See application file for complete search history.

(56) References Cited

U.S. PATENT DOCUMENTS

| | | | |
|---|---|---|---|
| 5,248,309 | A | 9/1993 | Serbiak et al. |
| 5,248,524 | A | 9/1993 | Soderlund |
| 5,324,278 | A | 6/1994 | Visscher et al. |
| 5,380,310 | A | 1/1995 | Mitrani |
| 5,422,169 | A | 6/1995 | Roe |
| 5,423,786 | A | 6/1995 | Fung et al. |
| 5,423,787 | A | 6/1995 | Kjellberg |
| 5,429,627 | A | 7/1995 | Johnson et al. |
| 5,441,442 | A | 8/1995 | Haisma et al. |
| 5,447,507 | A | 9/1995 | Yamamoto |
| 5,447,677 | A | 9/1995 | Griffoul et al. |
| 5,451,442 | A * | 9/1995 | Pieniak ................. A61F 13/535 |
| | | | 428/167 |
| 5,454,800 | A | 10/1995 | Hirt et al. |
| 5,460,623 | A | 10/1995 | Emenaker et al. |
| 5,556,392 | A | 9/1996 | Koczab |
| 5,562,646 | A | 10/1996 | Goldman et al. |
| 5,611,879 | A | 3/1997 | Morman |
| 5,649,916 | A | 7/1997 | Dipalma et al. |
| 5,674,214 | A | 10/1997 | Msscher et al. |
| 5,722,967 | A | 3/1998 | Coles |
| 5,728,084 | A | 3/1998 | Palumbo et al. |
| 5,733,274 | A | 3/1998 | Osborn |
| 5,769,836 | A | 6/1998 | Klemp |
| 5,776,121 | A | 7/1998 | Roe et al. |
| 5,821,179 | A | 10/1998 | Masaki et al. |
| 5,897,544 | A | 4/1999 | Ronnberg |
| 5,900,109 | A | 5/1999 | Sanders et al. |
| 5,910,137 | A | 6/1999 | Clark et al. |
| 6,024,822 | A | 2/2000 | Alper et al. |
| 6,050,984 | A | 4/2000 | Fujioka et al. |
| 6,068,620 | A | 5/2000 | Chmielewski |
| 6,140,550 | A | 10/2000 | Beihoffer et al. |
| 6,160,197 | A | 12/2000 | Lassen et al. |
| 6,162,959 | A | 12/2000 | O'Connor |
| 6,170,393 | B1 | 1/2001 | Hook et al. |
| 6,329,565 | B1 | 12/2001 | Dutkiewicz et al. |
| 6,372,952 | B1 | 4/2002 | Lash et al. |
| 6,417,120 | B1 | 7/2002 | Mitchler et al. |
| 6,475,199 | B1 | 11/2002 | Gann et al. |
| 6,506,959 | B2 | 1/2003 | Hamajima et al. |
| 6,566,578 | B1 | 5/2003 | Glaug et al. |
| 6,569,137 | B2 | 5/2003 | Suzuki et al. |
| 6,602,234 | B2 | 8/2003 | Klemp et al. |
| 6,613,955 | B1 | 9/2003 | Lindsay et al. |
| 6,632,209 | B1 * | 10/2003 | Chmielewski .... A61F 13/49406 |
| | | | 604/385.01 |
| 6,638,260 | B2 | 10/2003 | Mishima |
| 6,645,186 | B2 | 11/2003 | Otsubo |
| 6,652,499 | B1 | 11/2003 | Edgren et al. |
| 6,666,851 | B2 | 12/2003 | Otsubo et al. |
| 6,673,985 | B2 | 1/2004 | Mizutani et al. |
| 6,677,498 | B2 | 1/2004 | Chen et al. |
| 6,689,416 | B2 | 2/2004 | Delzer et al. |
| 6,733,484 | B2 | 5/2004 | Van Gompel et al. |
| 6,790,798 | B1 | 9/2004 | Suzuki et al. |
| 6,794,557 | B1 | 9/2004 | Klemp et al. |
| 6,797,360 | B2 | 9/2004 | Varona |
| 6,822,135 | B2 | 11/2004 | Soerens et al. |
| 6,852,101 | B2 | 2/2005 | Damaghi et al. |
| 6,878,138 | B2 | 4/2005 | Tsuji et al. |
| 6,888,044 | B2 | 5/2005 | Fell et al. |
| 6,902,552 | B2 | 6/2005 | Vangompel et al. |
| 6,955,667 | B1 | 10/2005 | Tanaka et al. |
| 6,964,803 | B2 | 11/2005 | Krautkramer et al. |
| 7,008,408 | B2 | 3/2006 | Otsubo |
| 7,022,114 | B2 | 4/2006 | Fernfors et al. |
| 7,090,667 | B2 | 8/2006 | Fell et al. |
| 7,108,916 | B2 | 9/2006 | Ehrnsperger et al. |
| 7,121,818 | B2 | 10/2006 | Driskell |
| 7,169,136 | B2 | 1/2007 | Otsubo et al. |
| 7,172,583 | B2 | 2/2007 | Otsubo et al. |
| 7,226,437 | B2 | 6/2007 | Sasaki et al. |
| 7,232,300 | B2 | 6/2007 | Walter et al. |
| 7,247,215 | B2 | 7/2007 | Schewe et al. |
| 7,294,591 | B2 | 11/2007 | Soerens et al. |
| 7,326,193 | B2 | 2/2008 | Shimada et al. |
| 7,344,522 | B2 | 3/2008 | Suzuki et al. |
| 7,378,566 | B2 | 5/2008 | Soerens et al. |
| 7,458,960 | B2 | 12/2008 | Otsubo et al. |
| 7,520,874 | B2 | 4/2009 | Koyama et al. |
| 7,615,039 | B2 | 11/2009 | Rosenfeld et al. |
| 7,662,460 | B2 | 2/2010 | Herfert et al. |
| 7,695,461 | B2 | 4/2010 | Rosenfeld et al. |
| 7,708,727 | B2 | 5/2010 | Woltman et al. |
| 7,717,150 | B2 | 5/2010 | Manabe et al. |
| 7,722,590 | B2 | 5/2010 | Tsuji et al. |
| 7,727,212 | B2 | 6/2010 | Sakai et al. |
| 7,767,875 | B2 | 8/2010 | Olson et al. |
| 7,772,457 | B2 | 8/2010 | Ohtsuka et al. |
| 7,811,270 | B2 | 10/2010 | Rosenfeld et al. |
| 7,842,021 | B2 | 11/2010 | Wood et al. |
| 7,847,145 | B2 | 12/2010 | Kurita et al. |
| 7,855,314 | B2 | 12/2010 | Hanao et al. |
| 7,884,259 | B2 | 2/2011 | Hanao et al. |
| 7,887,527 | B2 | 2/2011 | Hayashi et al. |
| 7,935,299 | B2 | 5/2011 | Walsh et al. |
| 7,955,536 | B2 | 6/2011 | Sawyer et al. |
| 7,959,622 | B2 | 6/2011 | Kudo et al. |
| 8,163,124 | B2 | 4/2012 | Moriura et al. |
| 8,173,858 | B2 | 5/2012 | Kuroda et al. |
| 8,178,035 | B2 | 5/2012 | Edvardsson et al. |
| 8,182,736 | B2 | 5/2012 | Edvardsson |
| 8,183,430 | B2 | 5/2012 | Hakansson et al. |
| 8,207,395 | B2 | 6/2012 | Soerens et al. |
| 8,251,966 | B2 | 8/2012 | Kudo et al. |
| 8,277,432 | B2 | 10/2012 | Bergstrom et al. |
| 8,361,047 | B2 | 1/2013 | Mukai et al. |
| 8,466,334 | B2 | 6/2013 | Takeuchi et al. |
| 8,480,387 | B2 | 7/2013 | Alkmin et al. |
| 8,556,875 | B2 | 10/2013 | Takahashi et al. |
| 8,591,490 | B2 | 11/2013 | Kudo et al. |
| 8,616,867 | B2 | 12/2013 | Brown et al. |
| 8,691,040 | B2 | 4/2014 | Yamamoto |
| 8,754,286 | B2 | 6/2014 | Bergstrom et al. |
| 8,852,381 | B2 | 10/2014 | Nhan et al. |
| 8,859,844 | B2 | 10/2014 | Takeuchi et al. |
| 8,871,123 | B2 | 10/2014 | De Carvalho et al. |
| 8,968,263 | B2 | 3/2015 | Watabe et al. |
| 8,998,871 | B2 | 4/2015 | Kuroda et al. |
| 9,056,034 | B2 | 6/2015 | Akiyama |
| 9,066,838 | B2 | 6/2015 | Hippe et al. |
| 9,072,634 | B2 | 7/2015 | Hundorf et al. |
| 9,216,116 | B2 | 12/2015 | Roe et al. |
| 9,238,089 | B2 | 1/2016 | Chmielewski et al. |
| 9,326,896 | B2 | 5/2016 | Schäfer et al. |
| 9,375,506 | B2 | 6/2016 | Konishi et al. |
| 9,468,566 | B2 | 10/2016 | Rosati et al. |
| 9,549,858 | B2 | 1/2017 | Yang |
| 9,730,843 | B2 | 8/2017 | Rosati et al. |
| 9,750,651 | B2 | 9/2017 | Bianchi et al. |
| 9,757,284 | B2 | 9/2017 | Tsang et al. |
| 9,782,305 | B2 | 10/2017 | Mukai et al. |

(56) References Cited

U.S. PATENT DOCUMENTS

| | | | |
|---|---|---|---|
| 9,782,306 B2 | 10/2017 | Tsang et al. | |
| 9,782,307 B2 | 10/2017 | Blessing et al. | |
| 9,789,009 B2 | 10/2017 | Joseph | |
| 9,789,011 B2 | 10/2017 | Roe et al. | |
| 9,789,012 B2 | 10/2017 | Chmielewski et al. | |
| 9,789,014 B2 | 10/2017 | Wright et al. | |
| 9,889,050 B2 | 2/2018 | Arayama et al. | |
| 9,913,763 B2 | 3/2018 | Ryu et al. | |
| 10,071,002 B2 | 9/2018 | Bianchi et al. | |
| 10,098,795 B2 | 10/2018 | Mukai et al. | |
| 10,137,039 B2 | 11/2018 | Stelzig et al. | |
| 10,137,040 B2 | 11/2018 | Ehrnsperger et al. | |
| 10,201,462 B2 | 2/2019 | Wright et al. | |
| 10,441,481 B2 | 10/2019 | Bianchi et al. | |
| 10,456,305 B2 | 10/2019 | Ehrnsperger et al. | |
| 10,543,130 B2 | 1/2020 | Raycheck et al. | |
| 10,675,191 B2 | 6/2020 | Suzuki et al. | |
| 10,687,994 B2 | 6/2020 | Chmielewski et al. | |
| 2001/0006089 A1 | 7/2001 | Ando et al. | |
| 2001/0039405 A1 | 11/2001 | Keuhn et al. | |
| 2002/0007165 A1 | 1/2002 | Proglhof et al. | |
| 2002/0133131 A1 | 9/2002 | Rangachari et al. | |
| 2003/0060792 A1 | 3/2003 | Harriz et al. | |
| 2003/0084983 A1 | 5/2003 | Rangachari et al. | |
| 2003/0098115 A1 | 5/2003 | Dodge et al. | |
| 2003/0129915 A1 | 7/2003 | Harriz | |
| 2003/0135176 A1 | 7/2003 | Delzer et al. | |
| 2003/0143376 A1 | 7/2003 | Toyoshima et al. | |
| 2003/0187413 A1 | 10/2003 | Fell | |
| 2003/0236512 A1 | 12/2003 | Baker | |
| 2004/0054342 A1 | 3/2004 | Newbill et al. | |
| 2004/0126543 A1* | 7/2004 | Potts | A61F 13/5323 |
| | | | 428/195.1 |
| 2004/0253894 A1 | 12/2004 | Fell et al. | |
| 2005/0124961 A1 | 6/2005 | Morman et al. | |
| 2005/0186351 A1 | 8/2005 | Fung et al. | |
| 2006/0004334 A1 | 1/2006 | Schlinz et al. | |
| 2006/0020250 A1 | 1/2006 | Chester et al. | |
| 2006/0040579 A1 | 2/2006 | Sheldon et al. | |
| 2006/0058747 A1 | 3/2006 | Nguyen et al. | |
| 2006/0184149 A1 | 8/2006 | Kasai et al. | |
| 2006/0204723 A1 | 9/2006 | Bentley et al. | |
| 2006/0206072 A1 | 9/2006 | Malakouti et al. | |
| 2006/0206074 A1 | 9/2006 | Bernal et al. | |
| 2006/0266467 A1 | 11/2006 | Mlinar | |
| 2007/0142802 A1 | 6/2007 | Suzuki | |
| 2007/0244455 A1 | 10/2007 | Hansson et al. | |
| 2008/0082075 A1 | 4/2008 | Morrell-Schwartz | |
| 2008/0167634 A1 | 7/2008 | Kouta et al. | |
| 2009/0087636 A1 | 4/2009 | Yasuda et al. | |
| 2010/0032860 A1 | 2/2010 | Hernandez et al. | |
| 2011/0152809 A1 | 6/2011 | Carlucci et al. | |
| 2011/0184365 A1 | 7/2011 | Röttger et al. | |
| 2011/0313384 A1 | 12/2011 | Akiyama | |
| 2012/0226253 A1 | 9/2012 | Urushihara | |
| 2012/0232508 A1 | 9/2012 | Urushihara | |
| 2012/0316524 A1 | 12/2012 | Thomann et al. | |
| 2013/0174959 A1 | 7/2013 | Kufner et al. | |
| 2013/0184666 A1 | 7/2013 | Sasayama et al. | |
| 2014/0276510 A1 | 9/2014 | Ducker et al. | |
| 2014/0308483 A1 | 10/2014 | Li | |
| 2015/0045756 A1 | 2/2015 | Wright et al. | |
| 2015/0065974 A1 | 3/2015 | Michiels et al. | |
| 2015/0174280 A1 | 6/2015 | Stelzig et al. | |
| 2015/0209196 A1 | 7/2015 | Li | |
| 2015/0282992 A1 | 10/2015 | Deng et al. | |
| 2015/0313769 A1 | 11/2015 | Dahl et al. | |
| 2015/0342796 A1 | 12/2015 | Bianchi et al. | |
| 2015/0342797 A1 | 12/2015 | Jackels | |
| 2015/0342798 A1 | 12/2015 | Jackels | |
| 2015/0342799 A1 | 12/2015 | Michiels et al. | |
| 2015/0342801 A1 | 12/2015 | Bianchi et al. | |
| 2016/0040337 A1 | 2/2016 | Dutkiewicz et al. | |
| 2016/0158401 A1 | 6/2016 | Tai et al. | |
| 2016/0235594 A1 | 8/2016 | Ehrnsperger et al. | |
| 2016/0235595 A1 | 8/2016 | Ehrnsperger et al. | |
| 2016/0235596 A1 | 8/2016 | Ehrnsperger et al. | |
| 2016/0235603 A1 | 8/2016 | Ehrnsperger et al. | |
| 2016/0235604 A1 | 8/2016 | Ehrnsperger et al. | |
| 2016/0235605 A1 | 8/2016 | Ehrnsperger et al. | |
| 2016/0270987 A1 | 9/2016 | Stiehl et al. | |
| 2017/0056255 A1 | 3/2017 | Fites et al. | |
| 2017/0102306 A1 | 4/2017 | Dagher et al. | |
| 2017/0128276 A1 | 5/2017 | Scaife | |
| 2017/0135870 A1 | 5/2017 | Kamphus | |
| 2017/0135871 A1 | 5/2017 | Kamphus | |
| 2017/0281423 A1 | 10/2017 | Panayotova et al. | |
| 2017/0312145 A1 | 11/2017 | Bianchi et al. | |
| 2017/0312146 A1 | 11/2017 | Bianchi et al. | |
| 2017/0312147 A1 | 11/2017 | Bianchi et al. | |
| 2018/0064583 A1 | 3/2018 | Van De Maele | |
| 2018/0185203 A1 | 7/2018 | Mukai et al. | |
| 2018/0207039 A1* | 7/2018 | Kreuzer | A61F 13/536 |
| 2018/0256415 A1 | 9/2018 | Miao et al. | |
| 2018/0344541 A1 | 12/2018 | Ito et al. | |
| 2019/0046368 A1 | 2/2019 | Peri et al. | |
| 2019/0053956 A1 | 2/2019 | Nakamura et al. | |
| 2019/0076307 A1 | 3/2019 | Takashima et al. | |
| 2019/0358097 A1 | 11/2019 | Chmielewski et al. | |
| 2020/0253796 A1 | 8/2020 | Chmielewski et al. | |
| 2020/0337914 A1 | 10/2020 | Onishi | |

FOREIGN PATENT DOCUMENTS

| | | | |
|---|---|---|---|
| CN | 1163100 A | 10/1997 | |
| CN | 1336868 A | 2/2002 | |
| CN | 1215825 C | 8/2005 | |
| CN | 200977230 Y | 11/2007 | |
| CN | 1676225 B | 11/2010 | |
| CN | 101061977 B | 6/2011 | |
| CN | 102438665 A | 5/2012 | |
| CN | 103007333 A | 4/2013 | |
| CN | 101641067 B | 5/2013 | |
| CN | 202984020 U | 6/2013 | |
| CN | 103300975 A | 9/2013 | |
| CN | 103491912 A | 1/2014 | |
| CN | 203417298 U | 2/2014 | |
| CN | 203436465 U | 2/2014 | |
| CN | 103637883 A | 3/2014 | |
| CN | 102361612 B | 6/2014 | |
| CN | 102573733 B | 7/2014 | |
| CN | 102573734 B | 7/2014 | |
| CN | 103892966 A | 7/2014 | |
| CN | 102083474 B | 8/2014 | |
| CN | 203790143 U | 8/2014 | |
| CN | 101849876 B | 9/2014 | |
| CN | 203815724 U | 9/2014 | |
| CN | 203885720 U | 10/2014 | |
| CN | 102781384 B | 11/2014 | |
| CN | 104161623 A | 11/2014 | |
| CN | 103282001 B | 12/2014 | |
| CN | 204016630 U | 12/2014 | |
| CN | 104394823 A | 3/2015 | |
| CN | 102700179 B | 4/2015 | |
| CN | 103327942 B | 4/2015 | |
| CN | 104540488 A | 4/2015 | |
| CN | 204260925 U | 4/2015 | |
| CN | 104602658 A | 5/2015 | |
| CN | 104605995 A | 5/2015 | |
| CN | 104723618 A | 6/2015 | |
| CN | 204501258 U | 7/2015 | |
| CN | 103006385 B | 10/2015 | |
| CN | 102378615 B | 1/2016 | |
| CN | 105530900 A | 4/2016 | |
| CN | 205163419 U | 4/2016 | |
| CN | 103249385 B | 5/2016 | |
| CN | 105722485 A | 6/2016 | |
| CN | 205286723 U | 6/2016 | |
| CN | 205359815 U | 7/2016 | |
| CN | 105853068 A | 8/2016 | |
| CN | 205494179 U | 8/2016 | |
| CN | 103269664 B | 9/2016 | |
| CN | 103402470 B | 10/2016 | |
| CN | 106038084 A | 10/2016 | |

(56) References Cited

FOREIGN PATENT DOCUMENTS

| | | | |
|----|------------|----|---------|
| CN | 103313683 | B | 2/2017 |
| CN | 106361506 | A | 2/2017 |
| CN | 205947928 | U | 2/2017 |
| CN | 205947929 | U | 2/2017 |
| CN | 104470477 | B | 4/2017 |
| CN | 106821603 | A | 6/2017 |
| CN | 106880445 | A | 6/2017 |
| CN | 206214292 | U | 6/2017 |
| CN | 106937903 | A | 7/2017 |
| CN | 106974774 | A | 7/2017 |
| CN | 107625583 | A | 1/2018 |
| CN | 107802410 | A | 3/2018 |
| CN | 207745262 | U | 8/2018 |
| CN | 109568012 | A | 4/2019 |
| CN | 109620550 | A | 4/2019 |
| CN | 109758305 | A | 5/2019 |
| CN | 209032878 | U | 6/2019 |
| CN | 209075162 | U | 7/2019 |
| CN | 110547917 | A | 12/2019 |
| CN | 110840657 | A | 2/2020 |
| CN | 212439076 | U | 2/2021 |
| DE | 3620077 | C2 | 2/1991 |
| DE | 202012013572 | U1 | 1/2018 |
| EP | 0348978 | A2 | 1/1990 |
| EP | 0442223 | B1 | 2/1995 |
| EP | 0606208 | B1 | 5/1996 |
| EP | 0549781 | B1 | 9/1996 |
| EP | 0768070 | A1 | 4/1997 |
| EP | 0746296 | B1 | 6/2001 |
| EP | 1032337 | B1 | 10/2004 |
| EP | 2591758 | A1 | 5/2013 |
| EP | 2679210 | A1 | 1/2014 |
| EP | 3047827 | B1 | 3/2018 |
| EP | 3042639 | B1 | 9/2018 |
| EP | 2656826 | B1 | 10/2018 |
| FR | 2604064 | B1 | 2/1991 |
| GB | 2246373 | A | 1/1992 |
| GB | 2272916 | A | 6/1994 |
| GB | 2306331 | A | 5/1997 |
| GB | 2366518 | A | 3/2002 |
| JP | 1993049658 | A | 3/1993 |
| JP | 1997313530 | A | 12/1997 |
| JP | 3145105 | B2 | 3/2001 |
| JP | 2004016373 | A | 1/2004 |
| JP | 2004329511 | A | 11/2004 |
| JP | 3607038 | B2 | 1/2005 |
| JP | 3705943 | B2 | 10/2005 |
| JP | 2006230714 | A | 9/2006 |
| JP | 3847680 | B2 | 11/2006 |
| JP | 3883915 | B2 | 2/2007 |
| JP | 4128029 | B2 | 7/2008 |
| JP | 4156171 | B2 | 9/2008 |
| JP | 4163133 | B2 | 10/2008 |
| JP | 4280187 | B2 | 6/2009 |
| JP | 4678632 | B2 | 4/2011 |
| JP | 4695332 | B2 | 6/2011 |
| JP | 4883924 | B2 | 2/2012 |
| JP | 4919734 | B2 | 4/2012 |
| JP | 5001099 | B2 | 8/2012 |
| JP | 2013042881 | A | 3/2013 |
| JP | 5175147 | B2 | 4/2013 |
| JP | 5329274 | B2 | 10/2013 |
| JP | 5372484 | B2 | 12/2013 |
| JP | 5374298 | B2 | 12/2013 |
| JP | 5789423 | B2 | 10/2015 |
| JP | 5926904 | B2 | 5/2016 |
| JP | 6062707 | B2 | 1/2017 |
| JP | 6073619 | B2 | 2/2017 |
| JP | 6074184 | B2 | 2/2017 |
| JP | 6148419 | B2 | 6/2017 |
| JP | 2017217468 | A | 12/2017 |
| JP | 6306450 | B2 | 4/2018 |
| JP | 2018050669 | A | 4/2018 |
| JP | 6382253 | B2 | 8/2018 |
| JP | 2018166941 | A | 11/2018 |
| JP | 6460828 | B2 | 1/2019 |
| JP | 6496567 | B2 | 4/2019 |
| JP | 2019141308 | A | 8/2019 |
| JP | 2019162300 | A | 9/2019 |
| JP | 2019187740 | A | 10/2019 |
| JP | 2019208849 | A | 12/2019 |
| JP | 2020000273 | A | 1/2020 |
| JP | 2020010851 | A | 1/2020 |
| WO | 2009150984 | A1 | 12/2009 |
| WO | 2012002557 | A1 | 1/2012 |
| WO | 2012105283 | A1 | 8/2012 |
| WO | 2012105284 | A1 | 8/2012 |
| WO | 2014084087 | A1 | 6/2014 |
| WO | 2015012155 | A1 | 1/2015 |
| WO | 2015129367 | A1 | 9/2015 |
| WO | 2015198662 | A1 | 12/2015 |
| WO | 2015198665 | A1 | 12/2015 |
| WO | 2016063638 | A1 | 4/2016 |
| WO | 2016104184 | A1 | 6/2016 |
| WO | 16115181 | A1 | 7/2016 |
| WO | 2017077750 | A1 | 5/2017 |
| WO | 2017110747 | A1 | 6/2017 |
| WO | 17171782 | A1 | 10/2017 |
| WO | 2018100650 | A1 | 6/2018 |
| WO | 2018112229 | A1 | 6/2018 |
| WO | 2018123684 | A1 | 7/2018 |
| WO | 2018173737 | A1 | 9/2018 |
| WO | 2019070009 | A1 | 4/2019 |
| WO | 2019092807 | A1 | 5/2019 |
| WO | 2019092810 | A1 | 5/2019 |
| WO | 2020117731 | A1 | 6/2020 |

OTHER PUBLICATIONS

Edana, "Superabsorbent", Jun. 14, 2019, https://www.edana.org/discover-nonwovens/how-they're-made/superabsorbents.

Google, "Core Issues for Diapers", Sep. 28, 2015,https://www.index17.ch/en/news/core-issues-for-diapers-thin-is-in-195.

* cited by examiner

MULTI-LAYER ABSORBENT CORES AND METHODS OF MANUFACTURE

TECHNICAL FIELD

The present disclosure is directed to absorbent bodies, and more particularly to multi-layered absorbent bodies for use in, for example, absorbent articles.

BACKGROUND OF THE DISCLOSURE

People rely on disposable absorbent products in their everyday lives, including such articles as adult incontinence products, enuresis pants, training pants, and diapers. Many manufacturers seek to better meet the needs of users of such products. For example, there is a need to further improve fit, discretion, and leakage protection for many products.

One important component of many absorbent articles are the absorbent bodies, such as absorbent cores, contained in such articles. These absorbent bodies are generally responsible for capturing and retaining liquid bodily exudates, thereby preventing the exudates from leaking out of the absorbent article and further retaining the liquid away from a wearer's skin, which helps to promote the health of the skin. Advances in the structure and performance of absorbent bodies to produce thinner products which uptake liquid more quickly and leak less are a continued important area of market desire.

SUMMARY OF THE DISCLOSURE

The present disclosure is directed to absorbent bodies, and more particularly to layered absorbent bodies for use in, for example, absorbent articles.

In a first embodiment, an absorbent garment may extend in a longitudinal and a lateral direction and comprise a bodyside liner, an outer cover, an absorbent body disposed between the bodyside liner and the outer cover, the absorbent body comprising: a top facing material layer, a bottom facing material layer, a lofty nonwoven reinforcing material disposed between the top facing material layer and the bottom facing material layer, absorbent material comprising superabsorbent material disposed between the top facing material layer and the bottom facing material layer and within the reinforcing material, and an acquisition material disposed between the absorbent body and the bodyside liner, and wherein a first side portion of the absorbent body and a second side portion of the absorbent body are folded onto a central portion of the absorbent body forming a folded absorbent body with a first folded portion and a second folded portion with a channel region disposed between the first folded portion and the second folded portion, and wherein the acquisition material spans across the channel region.

In a second embodiment an absorbent garment may extend in a longitudinal and a lateral direction and may comprise a bodyside liner, an outer cover, an absorbent body disposed between the bodyside liner and the outer cover, the absorbent body comprising: a top facing material layer, a bottom facing material layer, a lofty nonwoven reinforcing material disposed between the top facing material layer and the bottom facing material layer, absorbent material comprising superabsorbent material forming a plurality of spaced superabsorbent material lanes disposed between the top facing material layer and the bottom facing material layer and within the reinforcing material, wherein a first side portion of the absorbent body and a second side portion of the absorbent body are folded onto a central portion of the absorbent body forming a folded absorbent body with a first folded portion and a second folded portion with a channel region disposed between the first folded portion and the second folded portion, and wherein the superabsorbent material lanes spaced apart by a of distance between 5 mm and 15 mm and a combined width of the superabsorbent material lanes comprises between 40% and 60% of an overall width of the folded absorbent body; and an acquisition material disposed between the absorbent body and the bodyside liner, wherein the acquisition material spans across the channel region and is bonded into the channel.

In a third embodiment a method of forming an absorbent garment may comprise: moving a first facing material in a machine direction, moving a reinforcing material in the machine direction, the reinforcing material having a first side and a second side, applying superabsorbent material to the first side of the reinforcing material, the first side of the reinforcing material facing up in a vertical direction, reversing an orientation of the reinforcing material so that the first side of the reinforcing material faces down in the vertical direction, applying the first side of the reinforcing material to the first facing material, applying superabsorbent material to the second side of the reinforcing material, moving a second facing material in the machine direction, applying the second facing material to the second side of the reinforcing material to form an absorbent laminate comprising the first facing material, the reinforcing material, and the second facing material, folding a first side portion and a second side portion of the absorbent laminate onto a central portion of the absorbent laminate, the first side portion and the second side portion folded onto the central portion to form a channel region in the folded absorbent laminate, moving an acquisition material in the machine direction, coupling the acquisition material to the folded absorbent laminate such that the acquisition material spans across the channel region, and coupling the folded absorbent laminate and the acquisition material between a bodyside liner material and an outer cover material to form an absorbent garment.

The above summary of the present disclosure is not intended to describe each embodiment or every implementation of the present disclosure. Advantages and attainments, together with a more complete understanding of the disclosure, will become apparent and appreciated by referring to the following detailed description and claims taken in conjunction with the accompanying drawings.

BRIEF DESCRIPTION OF DRAWINGS

The disclosure may be more completely understood in consideration of the following detailed description of various embodiments in connection with the accompanying drawings, in which.

Figure 1:
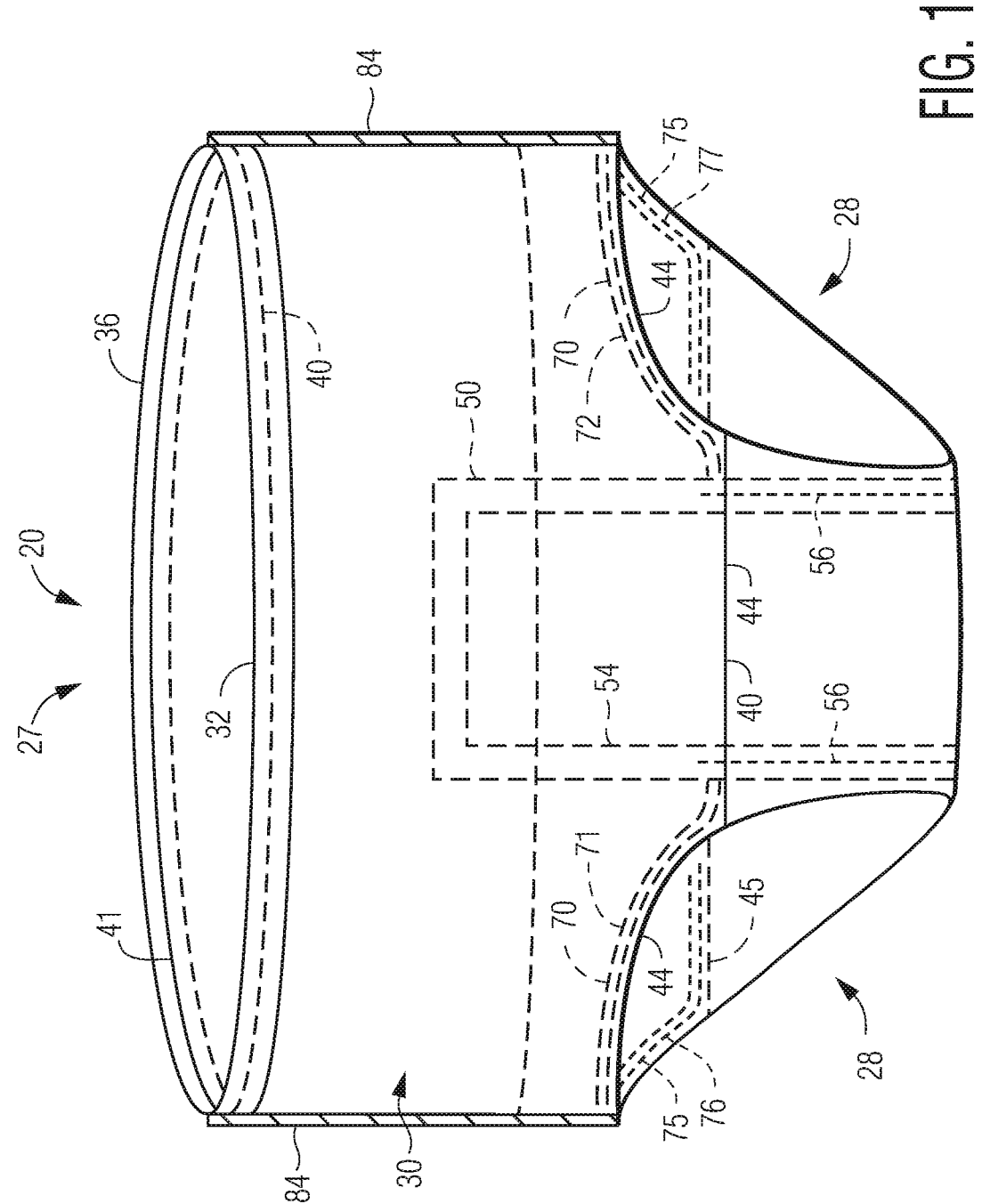
FIG. 1 is a perspective view of an exemplary absorbent garment in a closed configuration, according to aspects of the present disclosure.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the scope of the disclosure.

DETAILED DESCRIPTION OF THE DISCLOSURE

The present disclosure is directed to absorbent bodies, and more particularly to layered absorbent bodies for use in, for example, absorbent articles. The absorbent bodies of the present disclosure may be formed in a layered manner and comprise multiple layers. At least some of the absorbent bodies of the present disclosure may include superabsorbent material, and at least some of these bodies may include superabsorbent material disposed in a patterned fashion— for example in lanes of superabsorbent material. It has been found that such lanes of superabsorbent may allow for superior performance of the absorbent bodies of the present disclosure, in terms of faster first fluid intake time and rewet performance.

Further absorbent bodies of the present disclosure comprise layered absorbent bodies which have been folded. Particularly, it has been found that folding such layered absorbent bodies of the present disclosure to form a central channel or void further increases absorbent performance in terms of faster first fluid intake time and rewet performance. Additional aspects of such absorbent bodies are described in more detail below.

The following description should be read with reference to the drawings in which similar elements in different drawings are numbered the same. The description and the drawings, which are not necessarily to scale, depict illustrative embodiments and are not intended to limit the scope of the disclosure.

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

Each example is provided by way of explanation and is not meant as a limitation. For example, features illustrated or described as part of one embodiment or figure can be used on another embodiment or figure to yield yet another embodiment. It is intended that the present disclosure include such modifications and variations.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

Within the context of this specification, each term or phrase below will include the following meaning or meanings. Additional terms are defined elsewhere in the specification.

"Absorbent article" or "absorbent garment" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, diaper pants, training pants, youth pants, swim pants, incontinence products, absorbent feminine care products, and the like without departing from the scope of the present disclosure.

"Airlaid" refers herein to a web manufactured by an airlaying process. In the airlaying process, bundles of small fibers having typical lengths ranging from about 3 to about 52 mm are separated and entrained in an air supply and then deposited onto a forming screen, usually with the assistance of a vacuum supply. The randomly deposited fibers are then bonded to one another using, for example, hot air to activate a binder component or a latex adhesive. Airlaying is taught in, for example, U.S. Pat. No. 4,640,810 to Laursen, et al., which is incorporated herein in its entirety by reference thereto for all purposes.

"Bonded" refers to the joining, adhering, connecting, attaching, or the like, of two elements. Two elements will be considered bonded together when they are joined, adhered, connected, attached, or the like, directly to one another or indirectly to one another, such as when bonded to an intermediate element. The bonding can occur via, for example, adhesive, pressure bonding, thermal bonding, ultrasonic bonding, stitching, suturing, and/or welding.

"Bonded carded web" refers herein to webs that are made from staple fibers which are sent through a combing or carding unit which separates or breaks apart and aligns the staple fibers in the machine direction to form a generally machine direction oriented fibrous nonwoven web. This material may be bonded together by methods that can include point bonding, through air bonding, ultrasonic bonding, adhesive bonding, etc.

"Coform" refers herein to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff, and also superabsorbent particles, inorganic and/or organic absorbent materials, treated polymeric staple fibers and so forth. Some examples of such coform materials are disclosed in U.S. Pat. No. 4,100,324 to Anderson, et al., U.S. Pat. No. 4,818,464 to Lau, U.S. Pat. No. 5,284,703 to Everhart, et al., and U.S. Pat. No. 5,350,624 to Georger, et al., each of which are incorporated herein in their entirety by reference thereto for all purposes.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 50 percent of its relaxed length and which will recover, upon release of the applied force, at least 20 percent of its elongation. It is generally preferred that the elastomeric material or composite be capable of being elongated by at least 50 percent, more preferably by at least 100 percent, and still more preferably by at least 300 percent of its relaxed length and recover, upon release of an applied force, at least 50 percent of its elongation.

"Fibrous absorbent material" or "absorbent fibers" refers herein to natural fibers, cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber.

"Layer" when used in the singular can have the dual meaning of a single element or a plurality of elements.

"Machine direction" (MD) refers to the length of a fabric in the direction in which it is produced, as opposed to a "cross-machine direction" (CD) which refers to the width of a fabric in a direction generally perpendicular to the machine direction.

"Member" when used in the singular can have the dual meaning of a single element or a plurality of elements.

"Nonwoven fabric" or "nonwoven web" refers herein to a web having a structure of individual fibers or threads which are interlaid, but not in an identifiable manner as in a knitted fabric. Nonwoven fabrics or webs have been formed from many processes such as, for example, meltblowing processes, spunbonding processes, through-air bonded carded web (also known as BCW and TABCW) processes, etc.

"Spunbond web" refers herein to a web containing small diameter substantially continuous fibers. The fibers are formed by extruding a molten thermoplastic material from a plurality of fine, usually circular, capillaries of a spinneret with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542, 615 to Dobo, et al., and U.S. Pat. No. 5,382,400 to Pike, et al., which are each incorporated herein in their entirety by reference thereto for all purposes. Spunbond fibers are generally not tacky when they are deposited onto a collecting surface. Spunbond fibers may sometimes have diameters less than about 40 microns, and often between about 5 to about 20 microns.

"Superabsorbent polymer," "superabsorbent material", "SAP", or "SAM" shall be used interchangeably and shall refer to polymers that can absorb and retain extremely large amounts of a liquid relative to their own mass. Water absorbing polymers, which are classified as hydrogels, which can be cross-linked, absorb aqueous solutions through hydrogen bonding and other polar forces with water molecules. A SAP's ability to absorb water is based in par on iconicity (a factor of the ionic concentration of the aqueous solution), and the SAP functional polar groups that have an affinity for water. SAP are typically made from the polymerization of acrylic acid blended with sodium hydroxide I the presence of an initiator to form a poly-acrylic acid sodium salt (sometimes referred to as sodium polyacrylate). Other materials are also used to make a superabsorbent polymer, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. SAP may be present in absorbent garments in particle or fibrous form or as a coating or another material or fiber.

"Particle," "particulate," and the like, when used with the term "superabsorbent polymer," refer to the form of discrete units. The units can comprise flakes, fibers, agglomerates, granules, powders, spheres, pulverized materials, or the like, as well as combinations thereof. The particles can have any desired shape: for example, cubic, rod like polyhedral, spherical or semi-spherical, rounded or semi-rounded, angular, irregular, et cetera.

"Particulate superabsorbent polymer" and "particulate superabsorbent polymer composition" refer to the form of superabsorbent polymer and superabsorbent polymer compositions in discrete form, wherein the "particulate superabsorbent polymer" and "particulate superabsorbent polymer compositions" may have a particle size of less than 1000 μm, or from about 150 μm to about 850 μm.

"Polymer" includes, but is not limited to, homopolymers, copolymers, for example, block, graft, random, and alternating copolymers, terpolymers, etc., and blends and modifications thereof. Furthermore, unless otherwise specifically limited, the term "polymer" shall include all possible configurational isomers of the material. These configurations include, but are not limited to isotactic, syndiotactic, and atactic symmetries.

"Percent (%) by weight" or "% wt" as used herein and referring to components of the dry particulate superabsorbent polymer composition, is to be interpreted as based on the weight of the dry superabsorbent polymer composition, unless otherwise specified herein.

These terms may be defined with additional language in the remaining portions of the specification.

Figure 2:
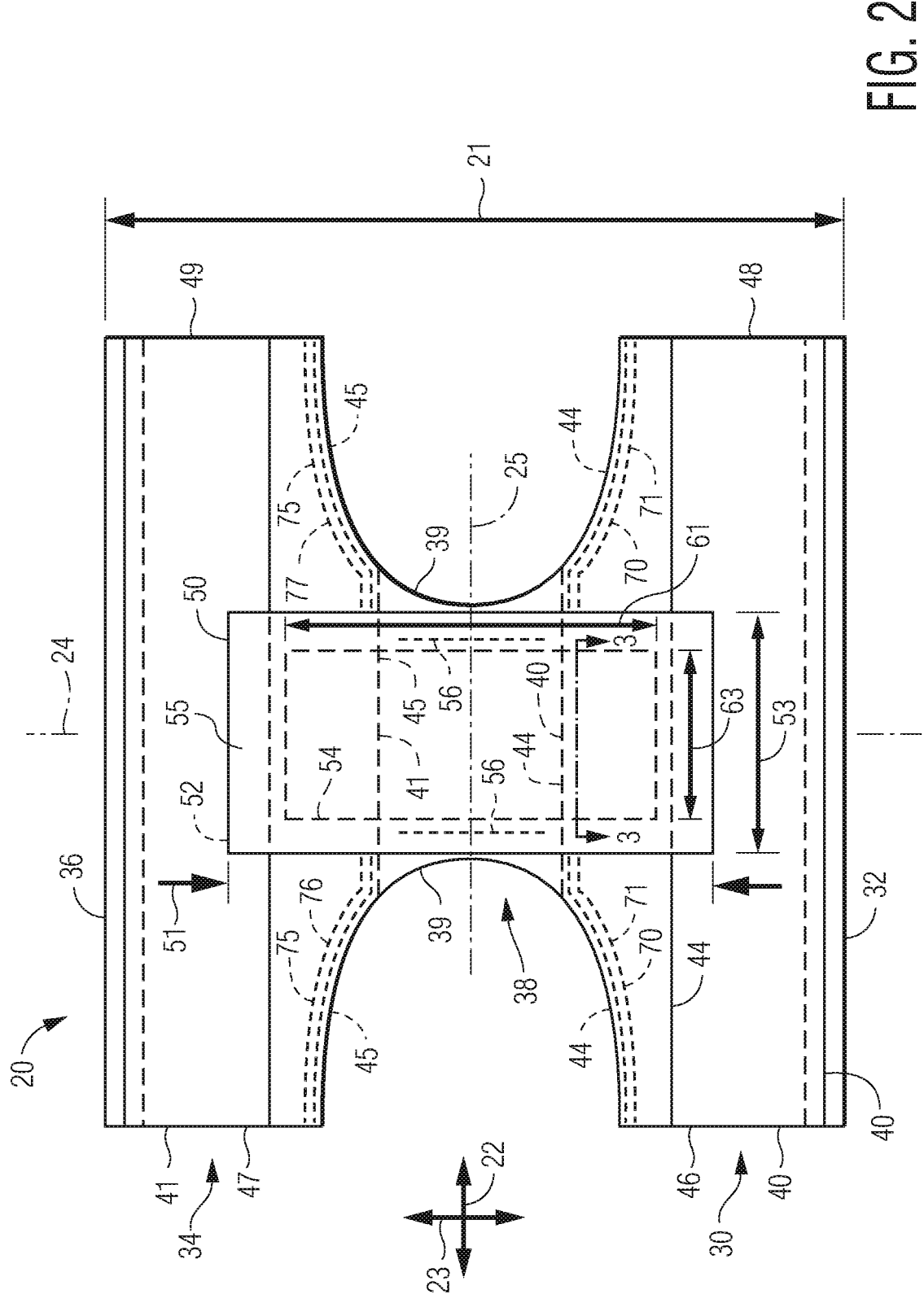
FIG. 2 is a plan view of the absorbent garment of FIG. 1 in an open and laid flat configuration.

Referring to FIGS. 1-2, a garment 20 extends along a longitudinal direction 23 and a lateral direction 22 perpendicular to the longitudinal direction 23. As used in describing the various embodiments of the garment 20, according to aspects of the present disclosure, the terms "longitudinal" and "lateral" have their customary meaning, as indicated by the central longitudinal axis 24 and the central lateral axis 25. The central longitudinal axis 24 lies in the plane of the garment when the garment is in a fully stretched and laid-flat condition, while the front and rear panels are separated, and is generally parallel to a vertical plane that bisects a standing wearer into left and right body halves when the garment is worn. The central lateral axis 25 lies in the plane of the garment and is generally perpendicular to the central longitudinal axis 24. The garment 20 has a front region 30 defining a front waist end edge 32, a rear region 34 defining a rear waist end edge 36, and a crotch region 38 positioned longitudinally between the front region 30 and the rear region 34. The crotch region 38 defines two laterally opposed crotch side edges 39. The garment 20 defines a garment length 21 that extends from the front waist end edge 32 to the rear waist end edge 36.

The garment 20 includes a front panel 40 which defines a front panel leg edge 44 spaced longitudinally inward from the front waist end edge 32, and first and second laterally opposed front panel side edges 46, 48. The garment 20 also includes a rear panel 41 which defines a rear panel leg edge 45 spaced longitudinally inward from the rear waist end edge 36, and first and second laterally opposed rear panel side edges 47, 49. "Longitudinally inward (or inboard)" as used to describe garment embodiments herein means in a direction longitudinally toward the central lateral axis 25. Likewise, "laterally inward (or inboard)" as used to describe garment embodiments herein means in a direction laterally toward the central longitudinal axis 24. The front panel 40 is longitudinally spaced apart from the rear panel 41. The front and rear panels 40 generally comprise elasticized materials so as to conform to a wearer's body.

A pair of side seams 84, 84 connects the front region 30 to the rear region 34, such that the garment 20 defines a waist opening 27 and a pair of leg openings 28. The side seams can be permanent but tearable, such as by way of adhesive, thermal, pressure, or ultrasonic bonding, or can be more readily releasable as well as refastenable, such as via the use of mechanical fastening elements.

The garment 20 may further include at least one front leg elastic member 70 disposed adjacent the front panel leg edge 44, and/or at least one rear leg elastic member 75 disposed adjacent the rear panel leg edge 45. Such leg elastic members 70 and/or 75 help to provide additional elastic support around the leg openings 28 to enhance the fit and leakage protection of the garment 20. Each leg elastic member 70, 75 can comprise a single ribbon, strand, or thread (or the like) of elastic material, or each can comprise two, three, or more ribbons, strands, or threads (or the like) of elastic material. In particular embodiments, the rear leg elastic member 75 and/or the front leg elastic member 70 extends laterally across the entire garment width. In other embodiments, such as that representatively illustrated in FIGS. 1 and 2, the rear leg elastic member 75 can comprise a pair of rear leg elastic members, such as first and second rear leg elastic members 76, 77 positioned on opposite sides of the absorbent composite 50. Similarly, the front leg elastic member 70 can comprise a pair of front leg elastic members, such as first and second front leg elastic members 71, 72 positioned on opposite sides of the absorbent composite 50. In preferred embodiments, such as that representatively illustrated in FIGS. 1 and 2, each rear leg elastic member 75 can comprise a plurality of elastomeric strands, and/or each front leg elastic member 70 can comprise a plurality of elastomeric strands.

In particular embodiments, an absorbent composite 50 is connected to and between the front panel 40 and the rear panel 41. The absorbent composite 50 may comprise a composite structure formed of a liquid impermeable barrier layer 52 defining a width 53 and a length 51, an absorbent body 54 comprising absorbent material, a liquid permeable liner 55, and/or crotch elastic members 56. As used herein, the term "absorbent material" may mean fibrous absorbent material, superabsorbent material (SAM), or a combination of both fibrous absorbent material and SAM. The absorbent body 54, in some embodiments, may comprise a layered structure that includes multiple regions of liquid-absorbing materials such as fibrous absorbent material and/or SAM. The absorbent body 54 defines a length 61 and a width 63. Further description of exemplary absorbent bodies 54 of the present disclosure is presented below with respect to FIG. 3.

It should be understood that the exemplary pant-like garment 20 is only one possible example of an absorbent garment or article which may be used with the described absorbent bodies 54 of the present disclosure. Such garments 20 as those shown in FIGS. 1 and 2 may be generally described as garments formed using a cross-machine direction (CD) manufacturing process. Alternative exemplary garments which may be used with the described absorbent bodies 54 may include those garments formed by a machine-direction (MD) manufacturing process. In general, the present disclosure is not meant to be limited to the specifically disclosed absorbent garments. Rather, the described absorbent bodies 54 may be used within any suitable chassis structure for retaining the described absorbent bodies 54 on a wearer. In even further contemplated embodiments, the described absorbent bodies 54 may not be used with any chassis structure at all. Rather, the absorbent bodies 54 may be constructed so as to be able to be placed directly in contact with a wearer's body—for example using body-adhesive disposed on a body-side surface of the absorbent bodies 54.

FIGS. 3A-4B are schematic depictions of a cross-section of exemplary absorbent bodies 54 of the present disclosure. For example, the bodies 54 of FIGS. 3A-4B may be cross-sections of the absorbent body 54 in FIG. 2, as viewed along line 5-5 of FIG. 2 and with any additional layers of the garment 20 removed. In general, the absorbent bodies 54 of the present disclosure may comprise multiple different materials, with some of the materials layered together to form the bodies 54.

Describing the specific embodiment of the absorbent body 54 shown in FIGS. 3A-4B, the exemplary absorbent bodies 54 comprises both a bottom covering material 101 and a top covering material 103 which are disposed about a reinforcing material 116. In at least some embodiments, the absorbent bodies 54 may further comprise a corewrap material (not shown).

The bottom covering material 101 and the top covering material 103 may be formed of any suitable materials. At least the top covering material 103 may be liquid permeable and may perform well in the uptake and wicking of fluid. In some embodiments, the bottom covering material 101 may also be liquid permeable and perform well in the uptake and wicking of fluid.

The covering materials 101 and/or 103 may include natural and/or synthetic fibers such as, but not limited to, polyester, polypropylene, acetate, nylon, polymeric materials, cellulosic materials and combinations thereof. In various embodiments, the covering materials 101 and/or 103 can be hydrophilic. In various embodiments, the covering materials 101 and/or 103 can be hydrophobic and can be treated in any manner known in the art to be made hydrophilic.

A few exemplary suitable materials for the covering materials 101 and/or 103 comprise tissue materials, spunbond and/or meltblown materials (e.g. spunbond-meltblown materials and spunbond-meltblown-spunbond materials), spunlace materials, HYDROKNIT® materials, which are a class of materials commercially available from Kimberly-Clark World Wide, Inc., airlaid materials, through-air bonded carded webs (TABCW), and coform materials. The covering materials 101, 103 may have basis weights ranging from between about 5 grams per square meter (gsm) and about 55 gsm.

According to some specific embodiments of the present disclosure, the top covering material 103 may be a tissue, SMS, or spunbond material having a basis weight of between about 7 gsm and about 20 gsm. In other embodiments, the top covering material 103 may be a coform, spunlace, or airlaid material having a basis weight of between about 35 gsm and about 55 gsm. According to other specific embodiments of the present disclosure, the bottom covering material 101 may be a coform, spunlace, airlaid, or Hydroknit® material having a basis weight between about 30 gsm and about 50 gsm.

According to further embodiments, the bottom covering material 101 may comprise a higher void volume than the top covering material 103. For instance, the top covering material may be a tissue, SMS, or spunbond material having a basis weight of between about 7 gsm and about 20 gsm while the bottom covering material 101 is a coform, spunlace, airlaid, or Hydroknit® material having a basis weight between about 30 gsm and about 50 gsm. Additionally, the bottom covering material 101 may comprise a material including naturally absorbent material, such as pulp fibers, while the top covering material 103 comprises a material which does not include naturally absorbent material. For example, the bottom covering material 101 may comprise a coform material having a basis weight between about 30 gsm and about 50 gsm while the top covering material 103 comprises an SMS or spunbond material having a basis weight of between about 7 gsm and about 20 gsm or a spunlace, airlaid, or Hydroknit® material having a basis weight between about 30 gsm and about 50 gsm. Although, all of the above described options are just some examples. Other suitable materials and/or materials having basis weights different than the above identified ranges may be used in other embodiments.

The reinforcing material 116 may help to provide some structural integrity to the bodies 54 and to assist in liquid uptake and distribution. Another benefit of the reinforcing material 116 is that it may help to stabilize absorbent material embedded within the reinforcing material 116. In general, the reinforcing material 116 may comprise a nonwoven material comprised of multiple individual fibers 117. For example, the reinforcing material 116 may be a spunbond material or a spunbond-meltblown-spunbond (SMS) material. In other embodiments, the nonwoven material may be a porous nonwoven material such as a TABCW or a chemically bonded nonwoven material or the like. The basis weight of the reinforcing material 116 may preferably be between about 15 gsm and about 60 gsm, or between about 25 gsm and about 55 gsm, or between about 30 gsm and about 50 gsm in other embodiments. In some specific embodiments, the reinforcing material 116 may be comprised substantially of polyolefin bi-component fibers, or polyolefin mixed bi-component and eccentric fibers, or just polyolefin eccentric fibers. In some specific preferred examples, a TABCW material may be used comprising between 60% to 80%, by weight, eccentric bi-component fibers (comprising polyethylene and polypropylene) having a denier of between about 3 and about 7 and between 20% and 40%, by weight, non-eccentric bi-component fibers (comprising polyethylene and polypropylene) having a denier of between about 1 and about 3. Although, it should be understood that these are just some exemplary materials. Other suitable materials may be used in other contemplated embodiments.

Although not required in all embodiments, where included, a corewrap material (not shown) may wrap at least partially around the top covering material 103, the reinforcing material 116, and the bottom covering material 101. In some configurations, the corewrap material may wrap partially around the materials 101, 103 and the reinforcing material 116 leaving a gap between ends of the corewrap material in what is sometimes called a "C-fold" configuration. In some of these embodiments, the gap between ends of the corewrap material may be adjacent the bottom covering material 101 while the gap between ends of the corewrap material may be adjacent the top covering material 103. In still further embodiments, the corewrap material may wrap fully around the materials 101, 103 and the reinforcing material 116 such that the materials 101, 103 and the reinforcing material 116 are fully enclosed by the corewrap material. The corewrap material may be bonded to one of the materials 101, 103 through adhesive seam beads or by adhesive sprayed onto the corewrap material and/or one or both of the materials 101, 103.

Such a corewrap material may be comprised of a tissue material, spunbond and/or meltblown material (e.g. spunbond-meltblown material or spunbond-meltblown-spunbond material), spunlace material, HYDROKNIT® material, airlaid material, through-air bonded carded web (TABCW), and coform material. Preferred corewrap materials may have a basis weight of between about 8 gsm and about 35 gsm. Although, it should be understood these are only exemplary materials and basis weights. In general, any suitable material at any suitable basis weight may be used.

In at least some embodiments where the corewrap material is not included, the top covering material 103 may be bonded directly to the bottom covering material 101, such as by adhesive seam-beads and/or adhesive spray, thereby enclosing the reinforcing material 116 without use of a corewrap material. For example, the top covering material 103 may wrap around the reinforcing material 116 to bond with the bottom covering material 101. Alternatively, both of the bottom covering material 101 and the top covering material 103 may wrap partially around the reinforcing material 116, or the bottom covering material 101 may wrap around the majority of the reinforcing material 116 to bond with the top covering material 103. The bottom covering material 101 or the top covering material 103 may wrap around the reinforcing material 116 and at least a portion of the other of the bottom covering material 101 and the top covering material 103 such that at least a portion of the other of the bottom covering material 101 and the top covering material 103 is enclosed. In such a configuration, the material 101 or 103 which wraps may form a C-fold or may fully enclose the other of the material 101, 103. In still other embodiments, the body 54 may only comprise a single covering material 101 or 103.

In such embodiments, the single covering material 101 or 103 may wrap around the reinforcing material 116 and be bonded to itself fully enclosing the reinforcing material 116. Of course, as shown in FIGS. 3A-4B, the materials 101, 103 may not appreciably wrap around the reinforcing material 116 at all such that side end edges of the materials 101, 103 and the reinforcing material 116 all approximately terminate at side edges of the body 54.

Figure 3A:
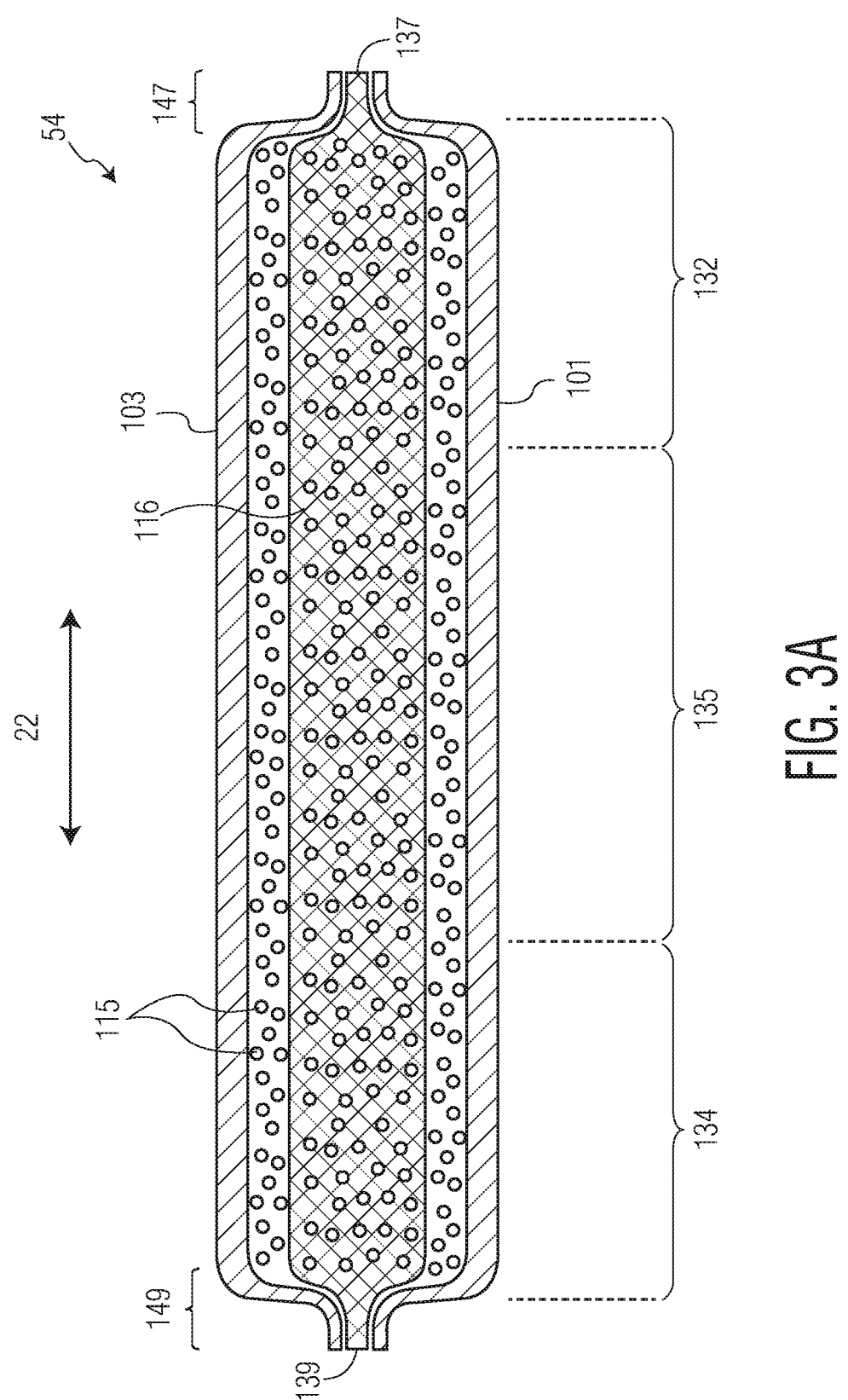
FIG. 3A is a cross-section view of an exemplary absorbent body, according to aspects of the present disclosure.
Figure 3B:
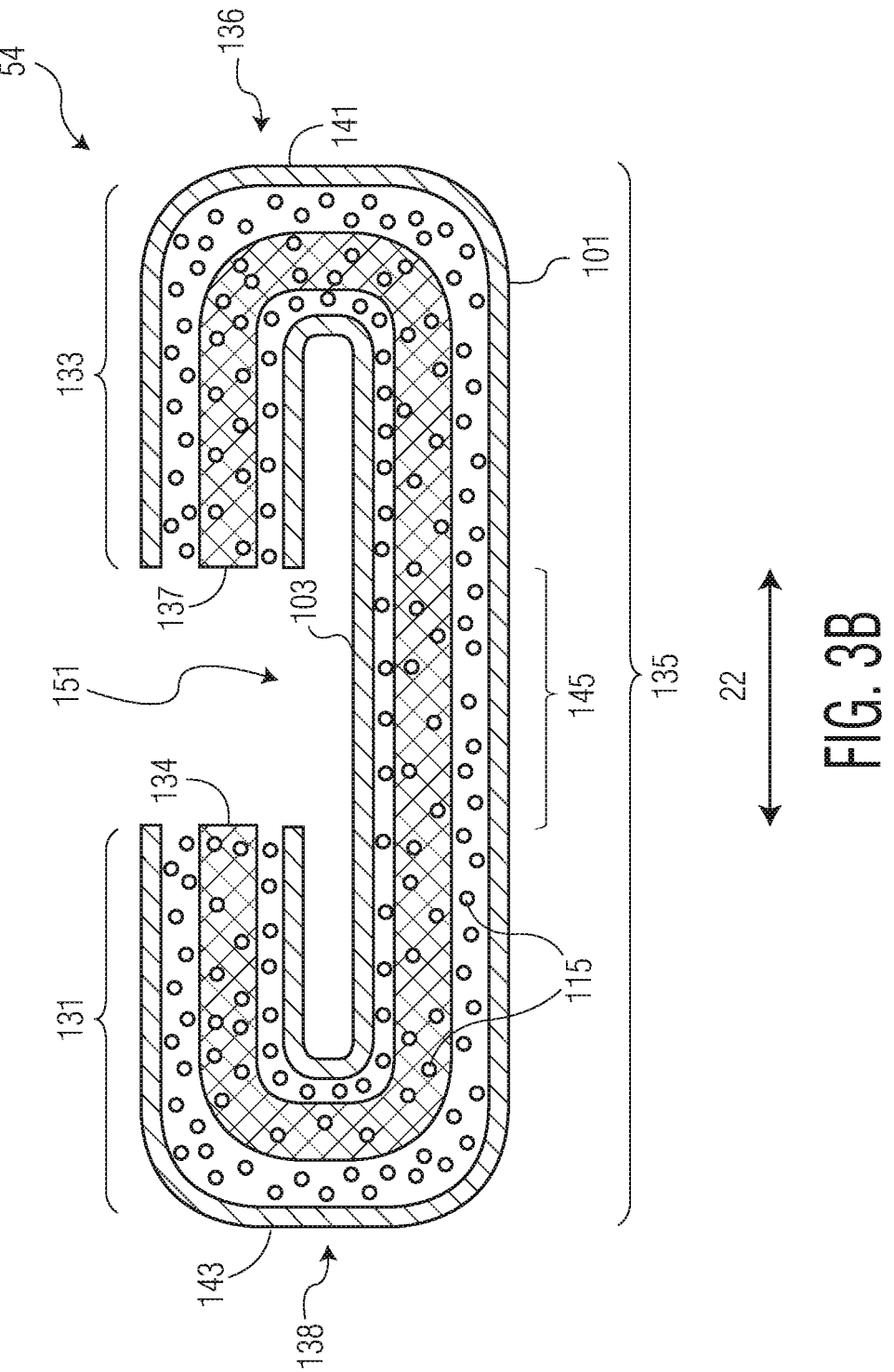
FIG. 3B is a cross-section view of an example of a folded absorbent body of FIG. 3A, according to aspects of the present disclosure.
Figure 4A:
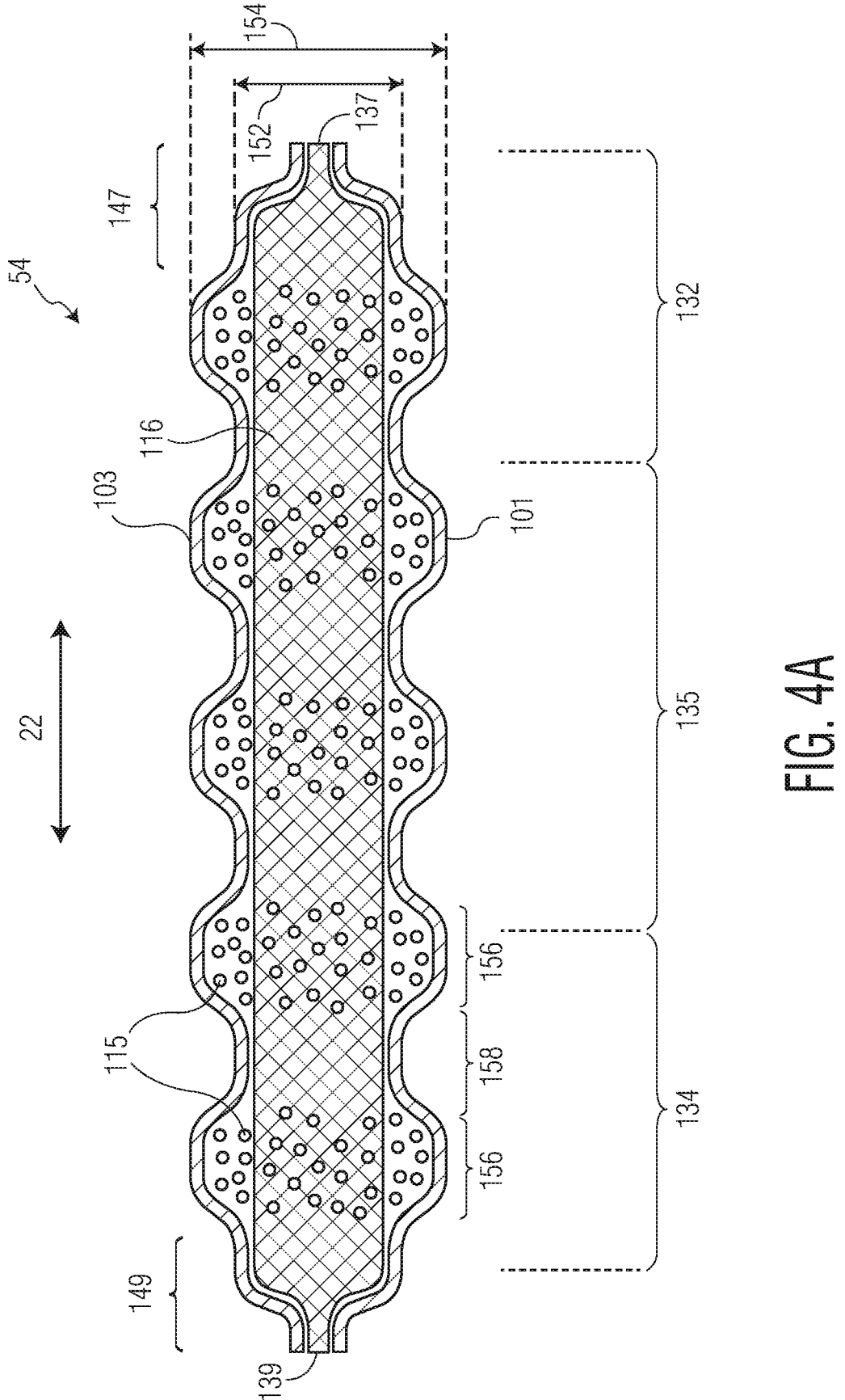
FIG. 4A is an cross-section view of a further exemplary absorbent body, according to aspects of the present disclosure.

Further embodiments, such as shown in FIGS. 3A and 4A, include where the bottom covering material 101, the top covering material 103, and the reinforcing material 116 are all applied in an overlying, stacked relationship and where the end edges 137, 139 of the bodies 54 are bonded to seal the edges 137, 139. For example, the end edges 137, 139 including the bottom covering material 101, top covering material 103, and reinforcing material 116 may be bonded together with heat, pressure, and/or ultrasonic energy to seal the end edges 137, 139 of the bodies 54. Such sealing of the end edges 137, 139 helps to prevent escape of any absorbent material contained within the bodies 54. Additionally, although not specifically depicted in FIGS. 3B, 4B, 5, and 6, it should be understood that the end edges 137, 139 of such folded absorbent bodies 54 of the present disclosure may have similarly sealed end edges 137, 139 as described here with respect to FIGS. 3A and 4A.

The absorbent bodies 54 of the present disclosure may also contain absorbent material to provide the absorbent bodies 54 with beneficial fluid intake and storage (e.g. fluid retention) qualities. For example, the absorbent bodies 54 comprise superabsorbent material disposed throughout the bodies 54, for example as depicted by SAM particles 115 in FIGS. 3A-6. In some embodiments, the absorbent material of bodies 54 may include absorbent material comprised of only superabsorbent material or may comprise both superabsorbent material and fibrous absorbent material (such as pulp fluff) in other embodiments. In further embodiments, the absorbent bodies 54 may comprise greater than about 80% SAM by weight of the total weight of absorbent material in the absorbent bodies 54. In still further embodiments, the absorbent bodies 54 may comprise greater than about 90% SAM by weight of the total weight of absorbent material in the absorbent bodies 54 or even 100% SAM by weight of the total weight of absorbent material in the absorbent bodies 54.

The embodiment of absorbent body 54 of FIGS. 3A and 3B contemplate where the SAM particles 115 are generally spread throughout the cross-section width of the body 54 (e.g. in the lateral direction 22). Further embodiments are contemplated, however, where the SAM particles 115 are localized within the absorbent body 54 in a pattern or within specific regions. In the particular embodiments of FIGS. 4A and 4B, the SAM particles 115 may be localized within particular lanes. For example, the SAM particles 115 may be localized within SAM lane regions 156, and each of the SAM lane regions 156 may be spaced from adjacent SAM lane regions 156 by a spacing region 158.

The widths of the distances 158 between the SAM lane regions 156 may be preferred to be between about 5 mm and about 15 mm. In more specific embodiments, the widths of the spacing regions 158 may be preferred to be between about 5 mm and about 10 mm or between about 5 mm and about 8 mm. At least some embodiments include where the width of the narrowest region 158 is greater than or equal to about 80% of the width of the widest SAM lane region 156. In further embodiments, the width of the narrowest region 158 is greater than or equal to the about 90% or greater than or equal to about 95% of the width of the widest SAM lane region 156. In alternative or additional embodiments, the combined values of the widths of the regions 158 of the bodies 54 may be greater than or equal to 80% of the combined values of the widths of the lane regions 156. In further embodiments, the combined values of the widths of the regions 158 may be greater than or equal to 85% or greater than or equal to 90% of the combined values of the widths of the lane regions 156. It has been found that relatively equal spacing for the widths of the SAM lane regions 156 and the widths of the regions 158, as well as relatively equal total amounts of the widths of the regions 156, 158, may be preferable to allow for sufficient fluid penetration throughout the reinforcing material 116 and expansion of the SAM particles within the reinforcing material 116 to achieve desired absorbent performance.

The width of the SAM lane regions 156 in the lateral or cross-direction 22 may be between about 5 mm and about 15 mm or between about 5 mm and about 10 mm. As described above, it is desirable in some embodiments for sufficient spacing between the SAM lane regions 156 for fluid penetration. Accordingly, in at least some embodiments, a combined width of the SAM lane regions 156 may be between about 25% and about 75% of an overall width of the absorbent body 54 (as measured in an un-folded state). In further embodiments, it may be preferable for the combined width of the SAM lane regions 156 to be between about 40% and about 60% of an overall width of the absorbent body 54.

According to another aspect of such embodiments of the absorbent bodies 54 of the present disclosure as shown in FIG. 4A, an overall thickness of the absorbent body 54 in a location of the SAM lane regions 156 may be generally greater than the overall thickness of the absorbent body 54 in a location where the SAM lane regions 156 are not present—for example in the regions between the SAM lane regions 156 defined by the spacing distances 158. It has been found that a preferred ratio of the overall height 152 of the absorbent body 54 between the SAM lane regions 156 and the overall height 152 of the absorbent body 54 at the SAM lane regions 156 is between about 1.2 and about 1.8. More specific embodiments include where the ratio of the overall height 152 of the absorbent body 54 between the SAM lane regions 156 and the overall height 152 of the absorbent body 54 at the SAM lane regions 156 is between about 1.3 and about 1.7 or between about 1.4 and about 1.6. SAM lane regions 156. It has been found that at these preferred ratios, the amount of SAM particles 115 present within the SAM lane regions 156 is generally sufficient to provide the absorbent bodies 54 with an appropriate retention capacity but not so much create lamination issues or spread out within the absorbent bodies 54 to reduce the widths of the distances 158.

Figure 4B:
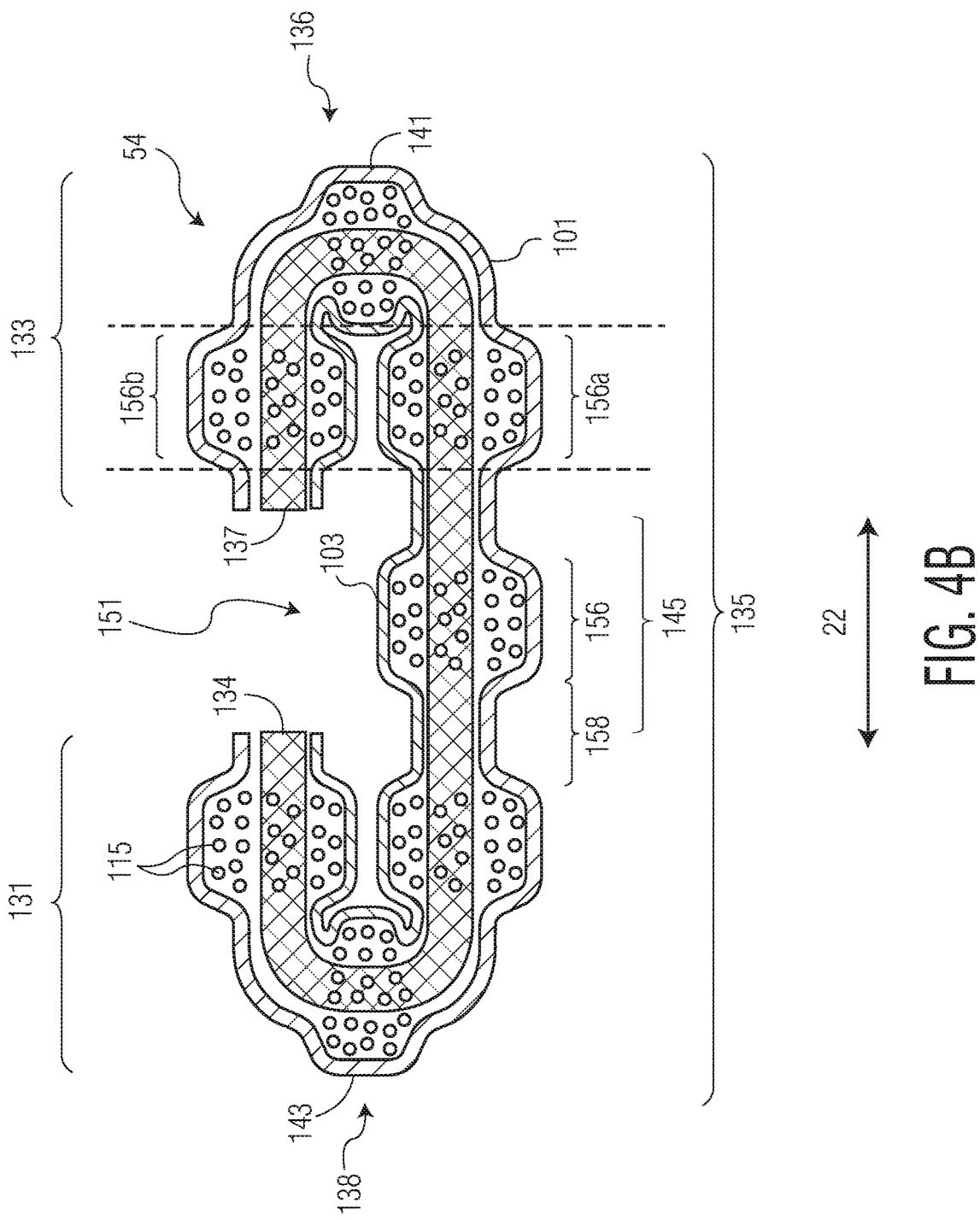
FIG. 4B is a cross-section view of an example of a folded absorbent body of FIG. 4A, according to aspects of the present disclosure.

While FIGS. 3A and 4A represent embodiments of absorbent bodies 54 according to aspects of the present disclosure which may be used as shown within absorbent articles, such as absorbent garment 20, further embodiments of absorbent bodies 54 of the present disclosure include bodies 54 which include one or more folds. For example, FIGS. 3B and 4B depict exemplary cross-sections of alternative, folded configurations of the absorbent bodies 54 of FIGS. 3A and 4A. Such folded absorbent bodies 54 of FIGS. 3B and 4B may alternatively be used within absorbent garment 20 of the present disclosure, as well as other absorbent articles. Accordingly, while FIGS. 5 and 6 depict exemplary cross-sections of the garment 20 of FIG. 2 including a folded absorbent body 54, it should be understood that any of the bodies 54 of the FIGS. 3A-4B can be utilized within garment 20.

Figure 5:
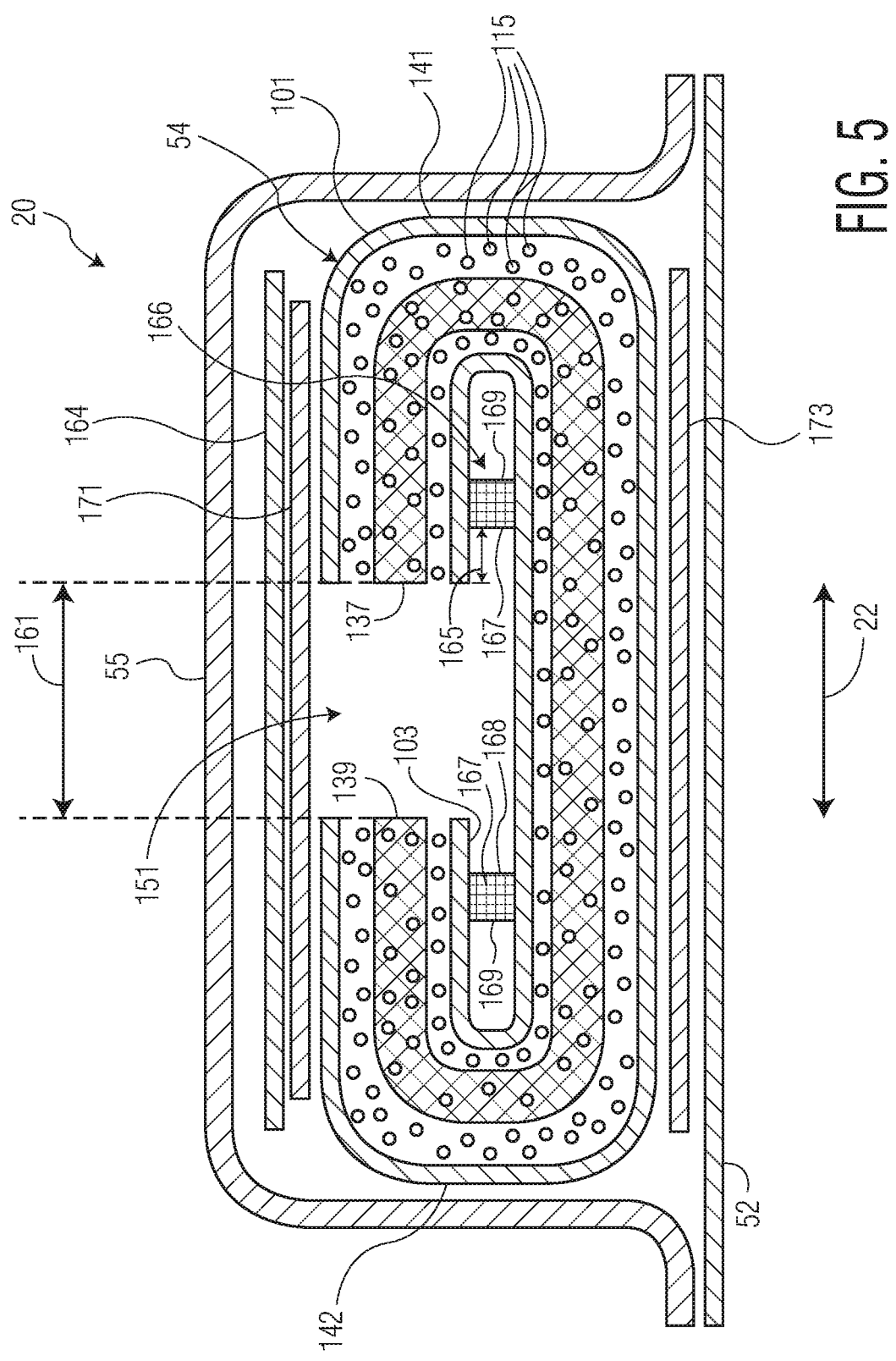
FIG. 5 is a cross-section view of the absorbent garment of FIG. 1 as viewed along line 5-5.
Figure 6:
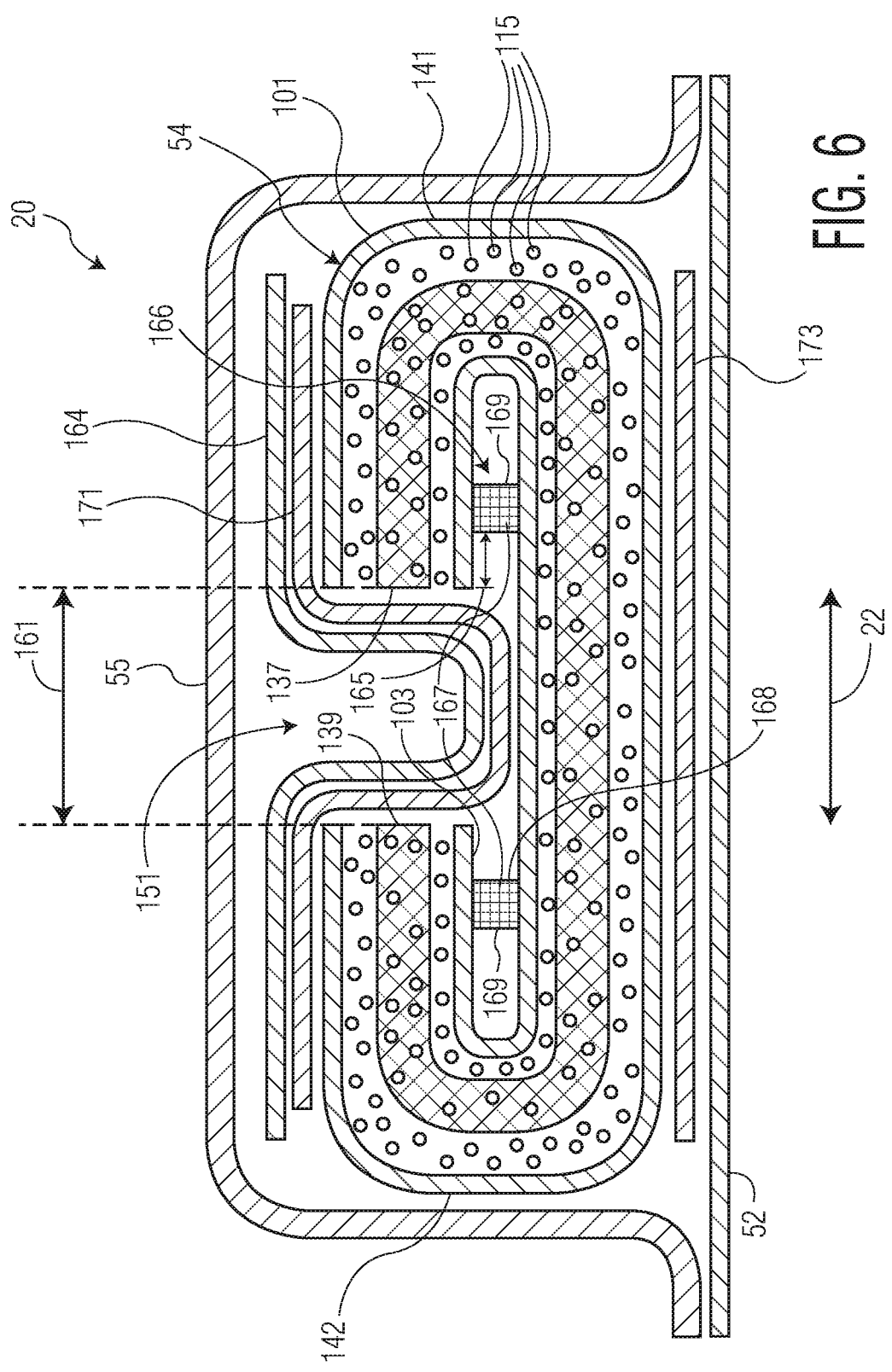
FIG. 6 is an alternative cross-section view of the absorbent garment of FIG. 1 as viewed along line 5-5.

As can be see, the absorbent bodies 54 of FIGS. 3B, 4B, 5, and 6 can include a first folded portion 131 and a second folded portion 133 as labeled in FIGS. 3B, 4B. For example, the bodies 54 may be formed having a planar configuration, for example as described with respect to FIGS. 3A and 4A, having a first end edge 137 and a second end edge 139. To arrive at the structures of the bodies 54 of FIGS. 3B, 4B, 5, and 6, a first side portion 132 including the first end edge 137 may be folded onto a central portion 135, forming first fold 136 located at a first longitudinally extending side edge 141 of the folded bodies 54. A second side portion 134 including second end edge 139 may also be folded onto the central portion 135, forming second fold 138 located at a second longitudinally extending side edge 142 of the folded bodies 54. In a preferred embodiment, such folded bodies 54, for example as depicted in FIGS. 5 and 6, may be placed within garment 20 where the side portions 132, 134, which are folded onto the central portion 135, are disposed on the top-side of the bodies 54 proximate the liner 55. Although, in other embodiments, the side portions 132, 134 may be folded onto the central portion 135 and disposed on the bottom-side of the body 54 such that the side portions 132, 134 are proximate the barrier layer 52 within the garment 20.

Where the side portions 132, 134 are folded onto central portion 135 leaving a gap between side portion end edges 143, 144, a channel region 151 is formed and defined by an unfolded central region 145 of the bodies 54. In the folded configuration, the bodies 54 comprise a width 162 (shown in FIG. 5) extending in the lateral direction 22 between the first longitudinally extending side edge 141 and the second longitudinally extending side edge 142. The channel region 151 may also have a channel width 161 extending in the lateral direction 22 between the side portion end edges 137, 139. It has been found that a desired channel width 162 is between about 30% and about 70% of the width 162. In more specific embodiments, the channel width 161 may be preferred to be between about 40% and about 60% of the width 162, or between about 35% and about 55% of the width 162.

In embodiments of the absorbent body 54 such as described with respect to FIG. 4A where the body 54 includes SAM lane regions 156 and spacing regions 158 between the SAM lane regions 156, the SAM lane regions 156 in the first folded portion 131 and the second folded portion 133 may be fully aligned, partially aligned, or fully un-aligned. In the example of FIG. 4B, it can be seen that a lateral extent of the SAM lane region 156*b* (e.g. a distance between the dashed lines of FIG. 4B) in the top portion of the second folded portion 133 is fully overlapping with a lateral extent of the SAM lane region 156*a* in the bottom portion of the second folded portion 133 in the lateral direction 22. The SAM lane region 156*a* can be seen located in the central portion 135, while the SAM lane region 156*b* is located in the second side portion 132 which was folded onto the central portions 135 to form the second folded portion 133. Such fully overlapping configurations may allow substantially superabsorbent material free regions to extend fully through a thickness of the absorbent body 54, thereby aiding in fluid uptake and distribution throughout the body 54.

In alternative embodiments, the lateral extent of the SAM lane region 156*b* in the top portion of the second folded portion 133 may only partially overlap with the lateral extent of the SAM lane region 156*a* in the bottom portion of the second folded portion 133 in the lateral direction 22. In such embodiments, the lateral extent of the SAM lane region 156*a* and the lateral extent of the SAM lane region 156*b* may overlap for a distance of between about 25% and about 75% of the lateral extent of the SAM lane region 156*a*. In further embodiments, the lateral extent of the SAM lane region 156*a* and the lateral extent of the SAM lane region 156*b* may overlap for a distance of between about 33% and about 66% or between about 40% and about 60% of the lateral extent of the SAM lane region 156*a*. Such partial overlapping of the SAM lane regions 156 in the folded portions 131, 133 may allow for at least some substantially superabsorbent material free regions to extend through the thickness of the body 54 while increasing opportunities for fluid to contact the superabsorbent material within the body 54, which can enhance particular absorbent performance parameters. In still further embodiments, there may be no overlap of the SAM lane regions 156 in the folded portions 131, 133. Such embodiments may where the SAM lane regions 156 in the folded portions 131, 133 are staggered in the lateral direction 22 may increase opportunities for fluid to contact the superabsorbent material within the body 54 as it penetrates in a vertical direction through the body 54, which can enhance particular absorbent performance parameters.

Prior to folding, adhesive may be applied to the top covering layer 103. For example, adhesives 166 and 168 may be applied to the top covering layer 103. The adhesives 166, 168 may have interior side edges 167 and exterior side edges 169, as well as a width in the lateral direction 22. The side portions 132, 134 may then be folded onto the central portion 135 such that the side portions 132, 134 cover the adhesives 166, 168 and bond the top covering material 103 to itself laterally outboard of the end edges 137, 139. The adhesives 166, 168 may be disposed relatively close to the end edges 137, 139 so as to interfere less with SAM swelling. Preferably, the distance 165 between interior side edges 167 of the adhesives 166, 168 and the end edges 137, 139 is less than about 10 mm, or less than about 7 mm, or less than about 5 mm. Further, it is preferred that the width of the adhesives 166, 168 in the lateral direction 22 is small so as to interfere less with fluid permeation throughout the bodies 54 of the present disclosure. According to preferred embodiments, a width of the adhesives 166, 168 in the lateral direction 22 is less than about 10 mm. In further embodiments, the width of the adhesives 166, 168 in the lateral direction 22 is less than about 7 mm, or less than about 5 mm, or less than about 3 mm.

The body 54 may further comprise an acquisition and/or distribution layer 164 (referred to herein as simply acquisition layer 164) disposed between the folded body 54 and the liner 55. The acquisition layer 164 may be coupled to the top-side of the folded body 54. In some of these embodiments, the acquisition layer 164 may be coupled to the folded body 54 by an adhesive layer 171. For example, an adhesive layer 171 may be applied to the acquisition layer 164 which in turn may be applied to the folded absorbent body 54. The acquisition layer 164 may preferably comprise materials similar to those described above with respect to top covering material 103. For example, acquisition layer 164 may preferably comprise tissue materials, spunbond and/or meltblown materials (e.g. spunbond-meltblown materials and spunbond-meltblown-spunbond materials), spunlace materials, HYDROKNIT® materials, airlaid materials, through-air bonded carded webs (TABCW), and coform materials and may have basis weights ranging from between about 5 grams per square meter (gsm) and about 55 gsm. According to some specific embodiments, the acquisition layer 164 may be a tissue, SMS, or spunbond material having a basis weight of between about 7 gsm and about 20 gsm or a coform, spunlace, or airlaid material having a basis weight of between about 35 gsm and about 55 gsm.

In the example of FIG. 5, the acquisition layer 164 is depicted spanning across the channel region 151 from the first end edge 137 to the second end edge 139 without contacting the top covering material 103, providing a gap between the acquisition layer 164 and the top covering material 103. Although the adhesive layer 171 is shown as spanning the channel region 151 as well, in at least some embodiments the adhesive layer 171 may be zoned so as to provide a gap between a first region of the adhesive layer 171 connecting the acquisition layer 164 to the bottom covering material 101 of the first folded portion 131 and a second region of the adhesive layer 171 connecting the acquisition layer 164 to the bottom covering material 101 of the second folded portion 133. In this manner, when the garment 20 is compressed, for example through further manufacturing steps or processes, the acquisition layer 164 may not become bonded into the channel region 151 and remain unconnected from the top covering material 103.

In alternative embodiments, the adhesive layer 171 may form a continuous adhesive region as shown in FIGS. 5 and 6. In at least some of these embodiments, the garment 20, including the folded body 54, may become compressed at one or more steps in the manufacturing process subsequent to application of the acquisition layer 164 to the folded absorbent body 54. In such embodiments, the acquisition layer 164 may be pressed into the channel region 151. Due to the presence of the continuous adhesive layer 171, the acquisition layer 164 may then become coupled to the folded absorbent body 54 within the channel region 151, as shown in FIG. 6. For example, the acquisition layer 164 may be coupled at least to the end edges 137, 139 and may further be coupled to the top covering layer 103 within the channel region 151. Such close contact between the acquisition layer 164 and the folded absorbent body 54 within the channel region 151 may be beneficial for superior acquisition and distribution of liquids by the garment into the folded absorbent body 54, thereby speeding up fluid intake times.

In at least some examples, the garment 20 may further include a bottom integrity sheet 173. The bottom integrity sheet 173 is generally disposed between the absorbent body 54 and the outer cover 52. The bottom integrity sheet 173 may help to contain the SAM particles 115 within the garment 20 and away from the outer cover 52 as well as to provide additional void volume and/or absorbency to the garment 20 for superior fluid handling properties. Accordingly, desirable materials for use as the bottom integrity sheet 173 include bulky materials and/or absorptive material including TABCW materials, spunlace materials, tissue materials, and coform materials. Such materials may have a basis weight of between about 30 gsm and about 75 gsm or between about 30 gsm and about 55 gsm.

Additionally, in order to maintain any of the absorbent bodies 54 of the present disclosure as a cohesive structure— for example at least those described above with respect to FIGS. 3A-6—and to assist in stabilizing the absorbent material within the bodies 54, the bodies 54 may comprise additional adhesives. In general, adhesive may be applied to different materials of the bodies 54 so as to form different adhesive layers. For example, some embodiments may include an adhesive layer between the bottom covering material 101 and the reinforcing material 116 (not shown)—applied to one or both of the reinforcing material 116 and the bottom covering material 101. Additionally, or alternatively, embodiments may include an adhesive layer between the top covering material 103 and the reinforcing material 116 (not shown)—applied to one or both of the reinforcing material 116 and the top covering material 103.

Figure 7A:
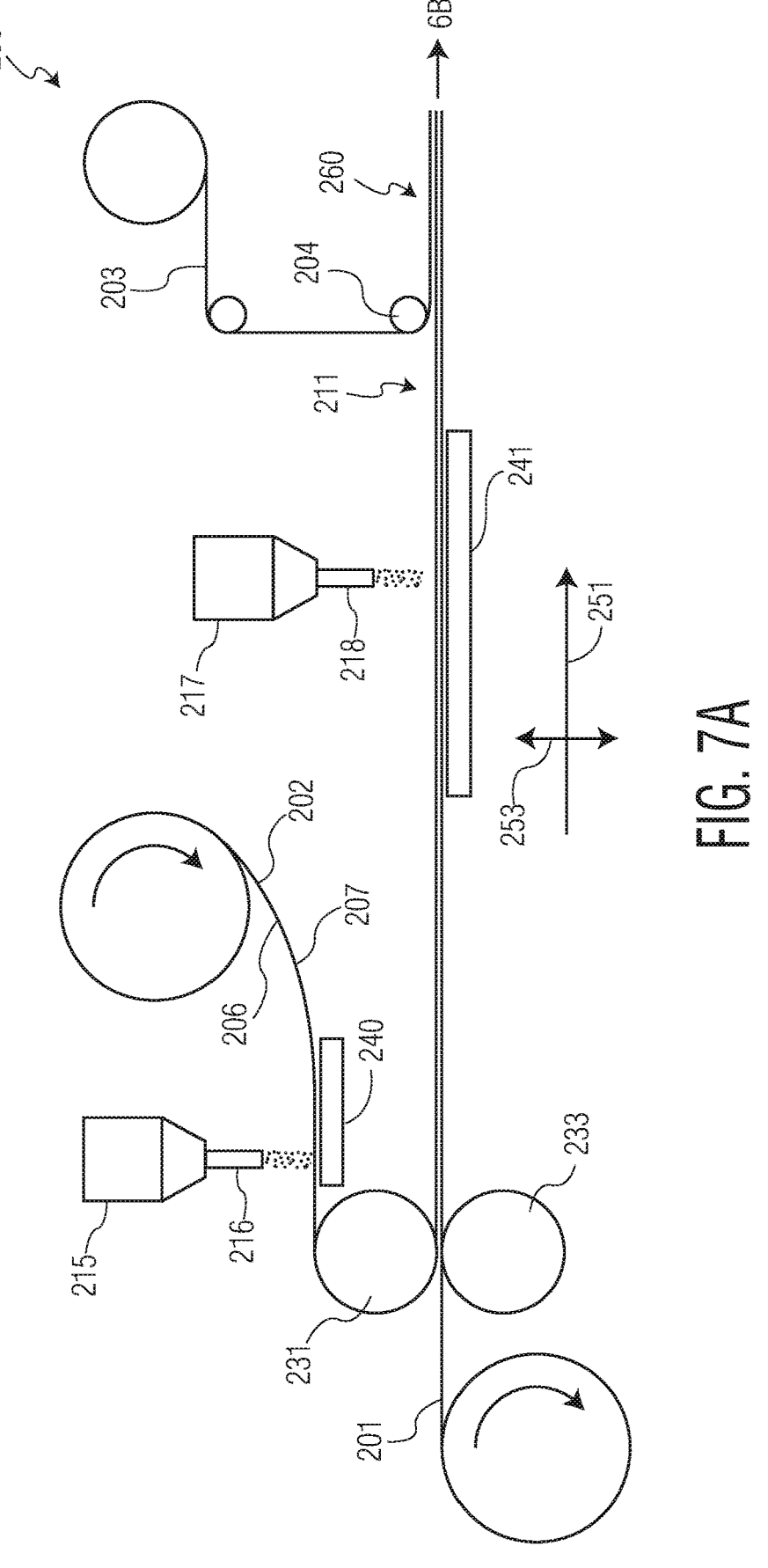
FIGS. 7A and 7B are schematic depictions of a process for forming absorbent bodies according to aspects of the present disclosure.
Figure 7B:
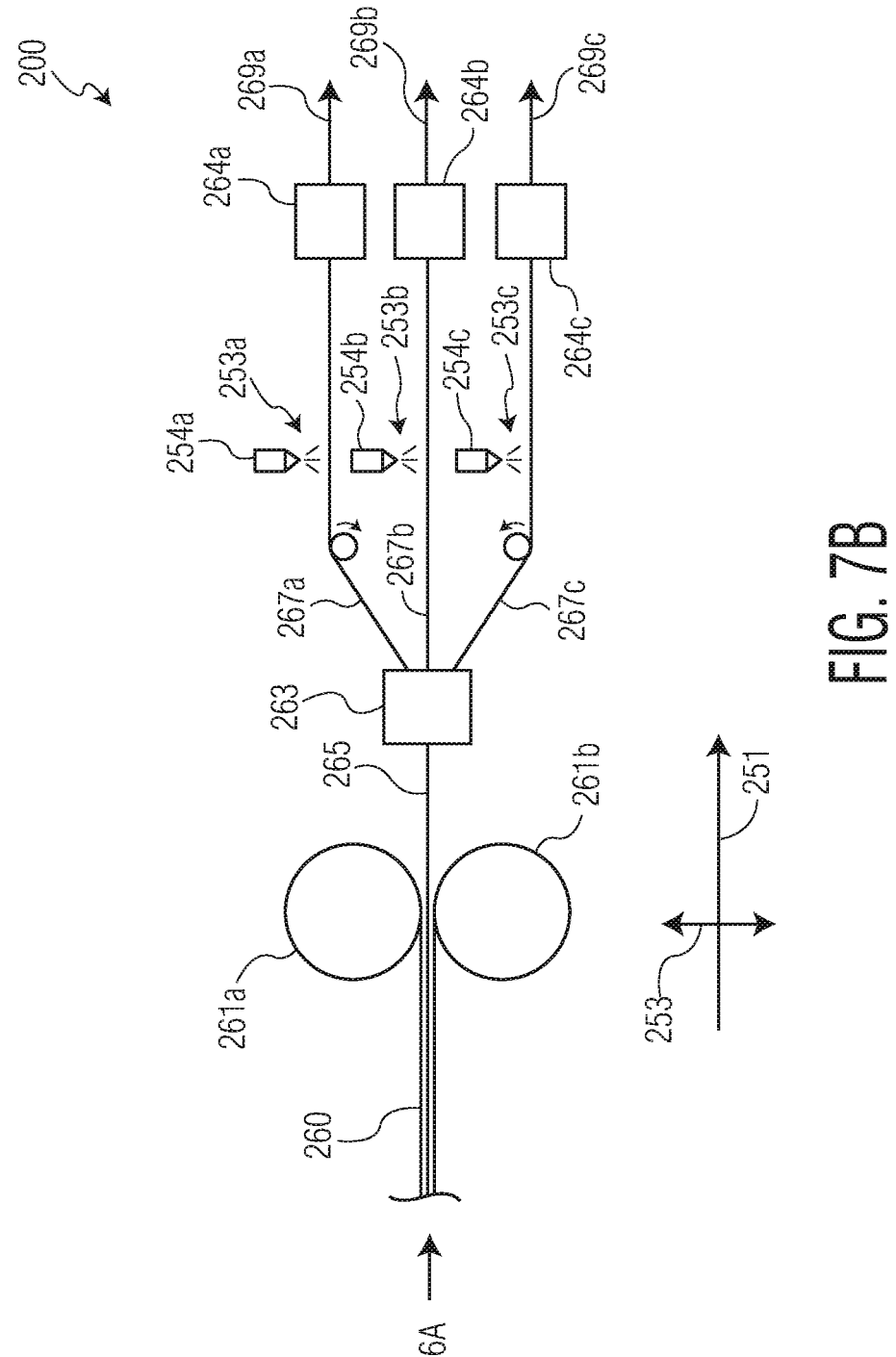

FIGS. 7A, 7B is a schematic depiction of a method 200 of manufacturing absorbent cores, such as the absorbent bodies 54 of the present disclosure. In a first step, a first covering material 201 having a top side and a bottom side may be unwound from a spool comprising material forming the first covering material 201. The first covering material 201 may correspond to the top covering material 103 described previously with respect to the absorbent bodies 54 of the present disclosure. Although, in other embodiments, the first covering material 201 may correspond to the bottom covering material 101 described previously.

As shown, a reinforcing material 202 having a top side and a bottom side may also be unwound from a spool and may further be coupled to the first covering material 201. The reinforcing material 202 may correspond to the reinforcing material 116 described above. Prior to coupling the reinforcing material 202 to the first covering material 201, superabsorbent material may be dispersed over and onto a first side of the reinforcing material 202. For example, the superabsorbent material may be stored in a hopper 215 and may be dispensed through conduit 216 to the first side of the reinforcing material 202. In some embodiments, the superabsorbent material (for example, SAM particles 115 as shown in FIGS. 3A-6) is dispensed in a metered fashion such that a designated amount of superabsorbent material is deposited onto the first side of the reinforcing material 202.

The superabsorbent material may be dispensed from the hopper 215 in such a fashion so as to achieve an add-on rate of between about 90 gsm to about 350 gsm. As the superabsorbent material contacts the first side of the reinforcing material 202, at least some of the superabsorbent material may penetrate into the reinforcing material 202. For example, the properties of the reinforcing material 202 may be such that voids between the fibers of the reinforcing material 202 are larger than at least some individual particles of the dispensed superabsorbent material, such that at least some particles of the dispensed superabsorbent material may filter into an interior of the reinforcing material 202.

Where at least some particles of the dispensed superabsorbent material may filter into an interior of the reinforcing material 202, such superabsorbent material particles may do so simply by gravity. In other embodiments, conveyer 240 could be a vacuum conveyer through which air is drawn through the first covering material 201 and the reinforcing material 202 and into the vacuum conveyer 240. In additional or alternative embodiments, the conveyer 240 may vibrate so as to vibrate the first covering material 201 and the reinforcing material 202 as the SAM is dispensed from the hopper 215. This addition of vacuum or vibration energy to the first covering material 201 and the reinforcing material 202 may help to increase the penetration of the dispensed superabsorbent material throughout the reinforcing material 202. However, in at least some embodiments the use of vacuum and/or vibration energy may not be needed to achieve a desired quantity of superabsorbent material stabilized within the reinforcing material 202.

Next, the reinforcing material 202, after having superabsorbent material deposited thereon, may be transported around guide roller 231 which changes the orientation of the first side of the reinforcing material 202, e.g. the side of the reinforcing material 202 to which superabsorbent material has been applied. As can be seen, the reinforcing material 202 may wrap around the guide roller 231 such that the orientation of the first side of the reinforcing material 202 is changed from facing up in the vertical direction 253 to facing down in the vertical direction 253. The guide roller 231 may further be utilized, in conjunction with a secondary roller 233, to form a nip to laminate the reinforcing material 202 to the first covering material 201.

The laminate of the first covering material 201 and the reinforcing material 202, now with a second side of the reinforcing material 202 facing up in the vertical direction 253, may be advanced in the process direction 251. A second application of superabsorbent material may be dispensed onto the laminate of the first covering material 201 and the reinforcing material 202 and, more particularly, onto the second side of the reinforcing material 202. For example, additional superabsorbent material may be stored in hopper 217 and may be dispensed through conduit 218 to the second side of the reinforcing material 202.

The superabsorbent material may generally be dispensed in a metered fashion such that a designated amount of superabsorbent material is deposited onto the second side of the reinforcing material 202. The superabsorbent material may be dispensed in such a fashion so as to achieve an add-on rate of between about 90 gsm to about 350 gsm. As with the first application of superabsorbent material to the first side of the reinforcing material 202, at least some of the particles of the superabsorbent material contacting the second side of the reinforcing material 202 may penetrate into the reinforcing material 202.

In some particular embodiments, conveyer 241 could be a vacuum conveyer. Although, in additional or alternative embodiments, the conveyer 241 may vibrate so as to vibrate the laminate of the first covering material 201 and the reinforcing material 202 first covering material 201 and the reinforcing material 202 as the superabsorbent material is dispensed from the hopper 217. Such added energy may help to increase the penetration of the dispensed superabsorbent material throughout the reinforcing material 202.

Next, a second covering material 203 may be unwound from a spool and brought to cover the partial core assembly 211 comprising the first covering material 201, the reinforcing material 202, and the applied superabsorbent material and form a full core assembly 260. In some embodiments, the second covering material 203 may be guided by guide roll 204. The second covering material 203 may correspond to the bottom covering material 101 in some embodiments, or the top covering material 103 in other embodiments.

At this point, the process 200 may further include cutting the full core assembly 260 into individual absorbent bodies 54 for use in absorbent articles, such as garment 20. However, process 200 may include further steps, for example in order to form absorbent cores such as those represented by folded bodies 54 of FIGS. 3B and 4B. For example, process 200 may further include transporting the formed full core assembly 260, which is a laminate of the first covering material 201, the reinforcing material 202, and the second covering material 203 in addition to the dispensed superabsorbent material, to a bonding apparatus—depicted as rolls

261*a*, 261*b*. The rolls 261*a*, 261*b* may apply heat, pressure, and/or ultrasonic energy to bond portions of the laminate 260, bonding each of the layers of the first covering material 201, the reinforcing material 202, and the second covering material 203 together, forming bonded assembly 265. Although shown as two rolls 261*a*, 261*b*, it should be understood that other typical bonding apparatuses which apply heat, pressure, and/or ultrasonic energy in the art may be substituted for the rolls 261*a*, 261*b*, such as blade-horn ultrasonic apparatuses.

In some examples according to method 200, the bonded assembly 265 may have a cross-direction width, e.g. a width in a dimension perpendicular to both the process direction 251 and the vertical direction 253, greater than a desired width of an absorbent body for use in an absorbent article, such as garment 20. In such embodiments, the bonded assembly 265 may be cut into discrete sections, such as sections 267*a*, 267*b*, and 267*c*. In embodiments where the absorbent bodies 54 are desired to be folded, the sections 267*a*, 267*b*, and 267*c* are advanced to folding apparatuses 264*a*, 264*b*, and 264*c* where each of the sections 267*a*, 267*b*, and 267*c* are folded. These folded sections 269*a*, 269*b*, and 269*c* may then be cut into individual absorbent bodies (such as absorbent bodies 54 of the present disclosure) and coupled to absorbent article chassis to form absorbent articles such as garment 20.

Where the resulting folded absorbent bodies 54 formed by the process 200 have adhesives bonding the top covering material 103 to itself in the folded portions of the bodies 54 (for example, adhesives 166, 168), the process 200 may further include applying adhesive to the sections 267*a*, 267*b*, and 267*c* prior to folding. For example, adhesive applicators 254*a*, 254*b*, 254*c* may apply adhesives 253*a*, 253*b*, 253*c* to each of the respective sections 267*a*, 267*b*, and 267*c*. The adhesives 253*a*, 253*b*, 253*c* are applied to the second covering material 203, which may correspond to the top covering layer 103 in some embodiments. The applied adhesives 253*a*, 253*b*, 253*c* may have the dimensions and spacing from end edges of the folded portions of the sections 267*a*, 267*b*, and 267*c* as described with respect to adhesives 166, 168.

Further, although not shown, it should be understood that adhesive may be applied at different portions of the method 200. For example, as described with respect to the structure of the absorbent bodies 54 of FIGS. 3A-6, adhesive layers may be present between the bottom covering material 101 and the reinforcing material 116 and/or between the top covering material 103 and the reinforcing material 116. Accordingly, the method 200 may further include a step of applying adhesive to one or both of the reinforcing material 202, before or after application of the superabsorbent material from the hopper 215, and the first covering material 201 (prior to lamination with the reinforcing material 202). The method 200 may additionally, or alternatively in different embodiments, include a step of applying adhesive to one or both of the reinforcing material 202, before or after application of the superabsorbent material from the hopper 217, and the second covering material 203 (prior to lamination with the reinforcing material 202).

Figure 8:
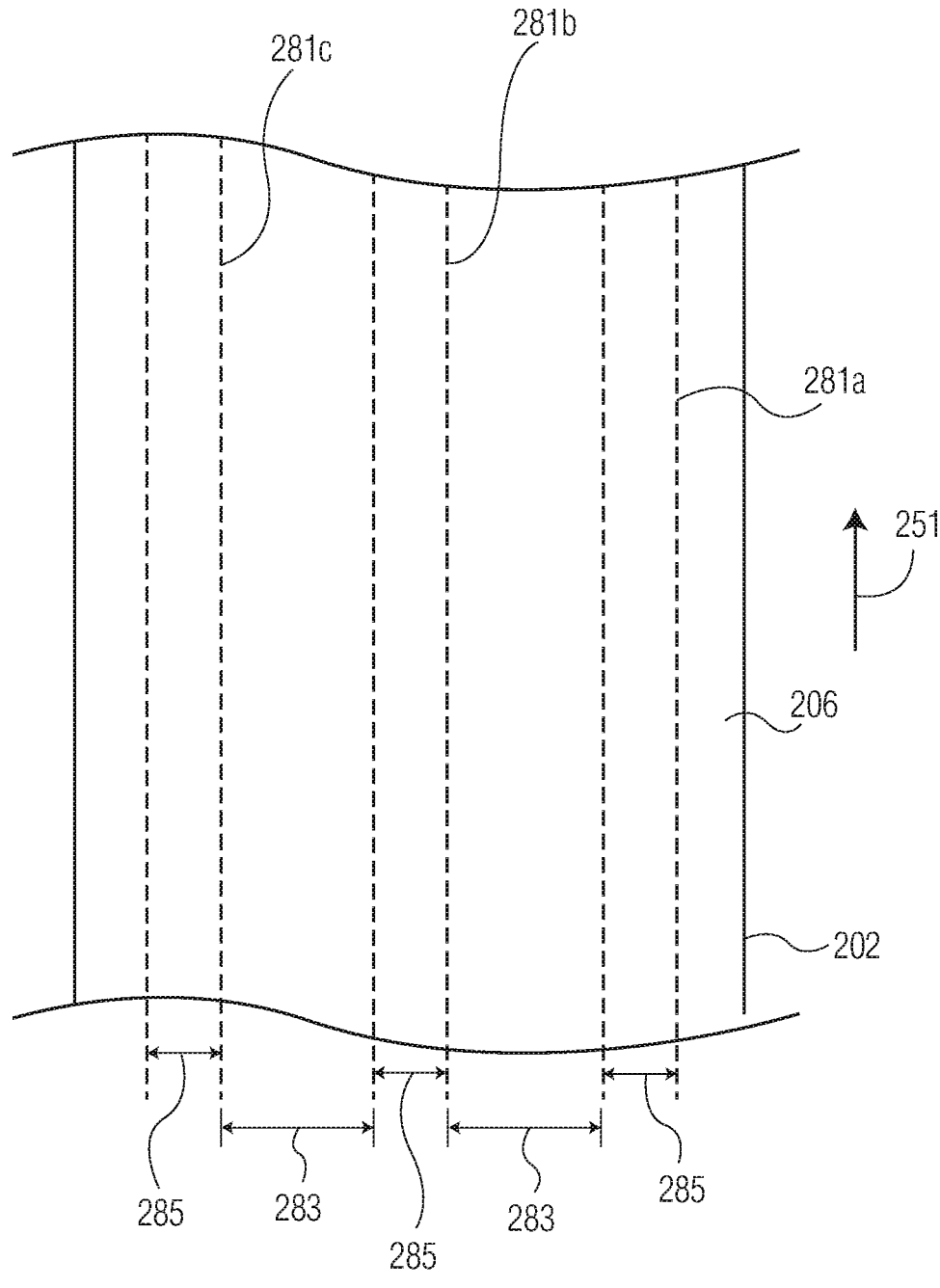
FIG. 8 is a top-plan view of a material used in the process depicted by FIGS. 6A and 6B, according to aspects of the present disclosure.

According to some aspects of the present disclosure, the superabsorbent material dispensed from the hopper(s) 215, 217 may be applied in a patterned manner. As depicted in FIG. 8, according to some embodiments, the superabsorbent material may be applied to the reinforcing material 202 in lanes, such as lanes 281*a-c*, extending in the process direction 251. Although FIG. 8 is described mainly with respect to the first side 206 of the reinforcing material 202, it should be understood that the same description applies to the second side 206 of the reinforcing material 202 where the superabsorbent material is deposited into lanes of superabsorbent material.

Lanes 281a-c represent deposition locations of superabsorbent material depositing onto the first side 206 of the reinforcing material 202. Each of the lanes 281a-c may have a width 285 and each of the lanes 281a-c may be spaced apart from adjacent lanes by distances 283. According to some embodiments of the present disclosure, the widths 285 of each of the lanes 281a-c may be between about 5 mm and about 20 mm. In more specific embodiments, the widths 285 of each of the lanes 281a-c may be between about 5 mm and about 15 mm or between about 5 mm and about 10 mm.

While the widths 285 of each of the lanes 281a-c may be the same in some embodiments, the widths 285 may vary between each individual lanes 281a-c. In some of these embodiments, however, the individual widths 285 may not vary too great. For example, the width 285 of the narrowest individual lane of the lanes 281a-c may be greater than or equal to 80% of the width 285 of the widest individual lane of the lanes 281a-c. In further embodiments, the width 285 of the narrowest individual lane of the lanes 281a-c may be greater than or equal to 85% of the width 285 of the widest individual lane of the lanes 281a-c or greater than or equal to 90% of the width 285 of the widest individual lane of the lanes 281a-c. It has been found that maintaining a relative closeness in widths 285 between all of the lanes 281a-c helps to produce superior fluid uptake and distribution properties in absorbent bodies 54 of the present disclosure.

The widths 283 of the spacing between each of the lanes 281a-c may also be preferred to be between about 5 mm and about 20 mm. In more specific embodiments, the widths 283 may be between about 5 mm and about 15 mm, between about 5 mm and about 10 mm, or between about 5 mm and about 8 mm. Of course, it need not be the case that each of the widths 283 between the lanes 281a-c is the same. However, it may be desirable for certain absorbent performance to ensure the widths 283 are relatively similar. Accordingly, in some embodiments, the lanes 281a-c are spaced apart an average distance, and wherein a difference between a smallest of the widths 283 and a largest of the widths 283 is less than 250% of the smallest of the widths 283. In further embodiments, it may be desirable for the spread of widths 283 to be smaller such that a difference between a smallest of the widths 283 and a largest of the widths 283 is less than 150% of the smallest of the widths 283.

It may also be preferred that the combined values of the widths 283 is relatively close to the combined widths 285 of each of the lanes 281a-c. For example, the combined values of the widths 283 may be greater than or equal to 80% of the combined values of the widths 285 of each of the lanes 281a-c. In further embodiments, the combined values of the widths 283 may be greater than or equal to 85% or greater than or equal to 90% of the combined values of the widths 285 of each of the lanes 281a-c. It has been found that having the total of the widths 283 be relatively close to the total of the widths 285 of each of the lanes 281a-c helps to ensure sufficient room for fast fluid uptake and distribution into the bodies 54 resulting in superior absorbent performance—for example with respect to fast first fluid intake times.

The regions of the reinforcing material 202 between the lanes 281a-c may be substantially devoid of absorbent material in some embodiments. For example, particularly with respect to embodiments such as described in FIGS. 10 and 11 where there is alignment between superabsorbent material lanes formed on the first side 206 of the reinforcing material 202 and superabsorbent material lanes formed on the second side 207 of the reinforcing material 202, the regions of the reinforcing material 202 between the lanes 281a-c may have much less superabsorbent material disposed in these regions than superabsorbent material disposed within the superabsorbent material lanes. As used herein, the term substantially devoid of absorbent material means that a region has an amount of absorbent material (for example, superabsorbent material) that is less than 10% of an average basis weight of the absorbent material of the structure. For example, when considering a formed absorbent body 54 having an average basis weight of superabsorbent material of 350 gsm, regions of the absorbent body 54 having a basis weight of superabsorbent material of less than 35 gsm may be considered to be substantially devoid of superabsorbent material.

Of course, while FIG. 8 depicts only three lanes of superabsorbent material 281a-c, any suitable number of lanes of superabsorbent material may be formed. In further embodiments, greater than five lanes of superabsorbent material may be formed according to process 200. In still further embodiments, greater than seven, greater than ten, greater than fifteen, greater than twenty, or greater than twenty-five lanes of superabsorbent material may be formed according to process 200. In at least some of these embodiments, the cross-direction width of the reinforcing material 202 (e.g. width of the reinforcing material 202 in the direction 255) may be greater than a desired width of an absorbent body for use in an absorbent article. In such embodiments, as described previously, the reinforcing material 202 may be cut into individual sections and each of the individual sections formed into discrete absorbent bodies. In these embodiments, the number of lanes of superabsorbent material applied to the reinforcing material 202 may be greater than the number of lanes of superabsorbent material disposed within an absorbent body 54 of the present disclosure. As one illustrative example, the process 200 may include applying twenty-one discrete lanes of superabsorbent material to the reinforcing material 202. The reinforcing material 202 may then be cut into three distinct sections whereby seven of the discrete lanes of superabsorbent material are disposed within each of the distinct sections. Accordingly, the absorbent bodies 54 resulting from this embodiment of process 200 would have seven lanes of superabsorbent material each.

Figure 9:
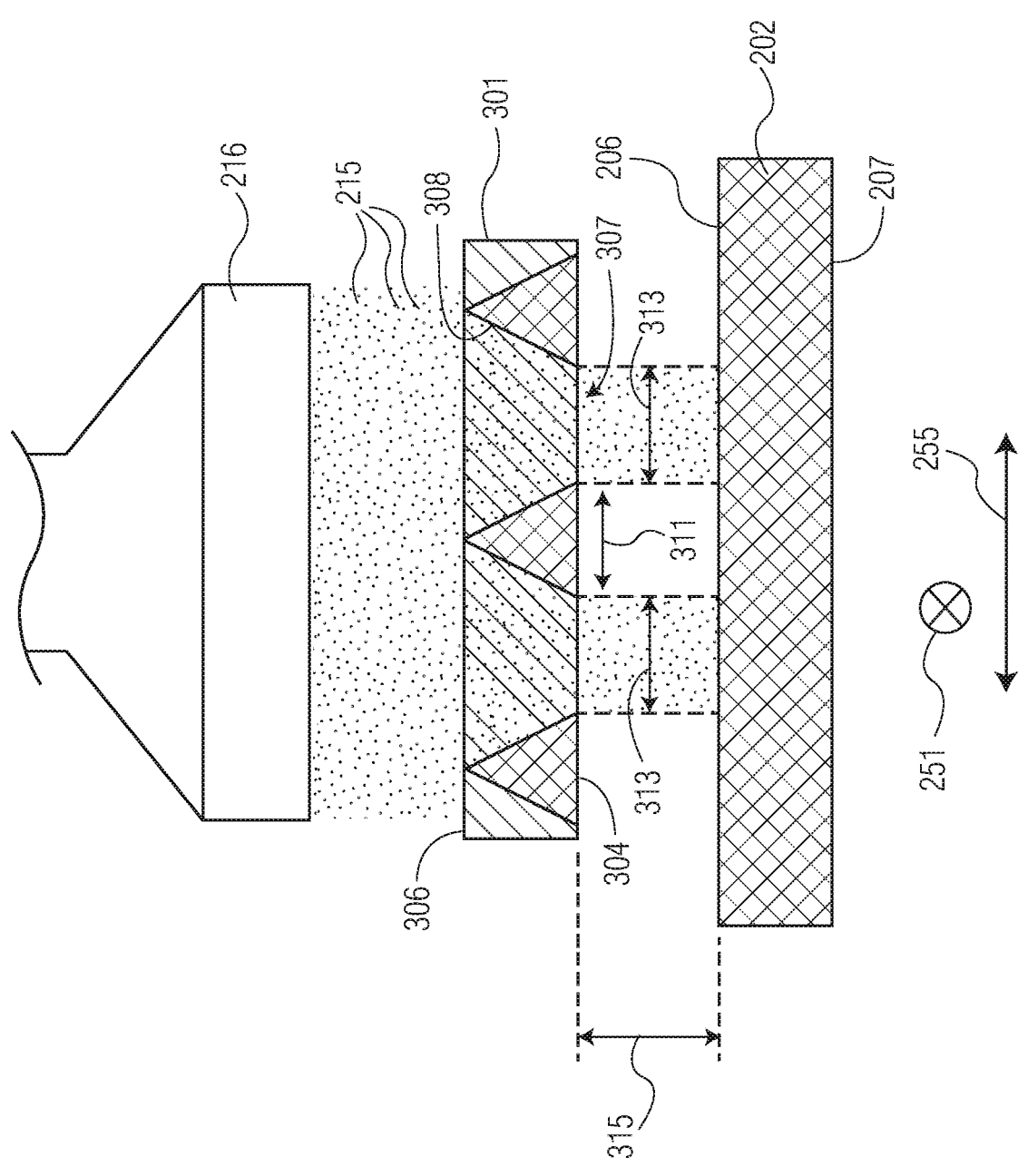
FIG. 9 is a schematic depiction of an exemplary particulate material deposition step in the process depicted by FIGS. 6A and 6B.

The widths 285 may represent a width of a lane of superabsorbent material as it contacts the first side 206 of the reinforcing material 202. Alternatively, where a masking component, such as mask member 301 shown in FIG. 9, is used to produce such lanes of superabsorbent material, the widths 285 may be a cross-direction 255 width of apertures 307 disposed in the bottom 304 of the mask member 301—represented by width 313 in FIG. 9. In some embodiments, the superabsorbent material depositing onto the first side 206 of the reinforcing material 202, as shown in FIG. 9, may not spread in the cross-direction 255 while falling between the bottom 304 of the mask member 301 and the first side 206 of the reinforcing material 202. In such instances, the width 285 of a lane of SAM as it contacts the first side 206 of the reinforcing material 202 and the cross-direction 255 width 313 of apertures 307 disposed in the bottom 304 of the mask member 301 are the same. Likewise, the widths 311 of the portions of the mask member 301 between the apertures 307 may correspond to the widths 283 representing the spacing between lanes of superabsorbent material.

Where employed, the mask member 301 may be positioned a distance 315 away from the first side 206 of the reinforcing material 202. The mask member 301 should be positioned close to the first side 206 of the reinforcing material 202 so that the superabsorbent material dispensing through the mask member 301 does not spread too great a distance in the cross-direction 255 in order to maintain distinction between the regions having superabsorbent material (e.g. the lanes 281*a-c*) and the regions without superabsorbent material (e.g. the spaces between the lanes 281*a-c*). In preferred embodiments, the distance 315 is between about 3 mm and about 20 mm. In more preferred embodiments, the distance 315 is between about 5 mm and about 15 mm, or between about 5 mm and about 10 mm.

The mask member 301 may comprise tapered internal walls 308 extending from the top side 306 of the mask member 301 to the bottom 307 side of the mask member 301, terminating at apertures 307 in the bottom side 307. The tapered internal walls 308 may funnel the SAM dispensed from the conduit 216, which typically comes out in an even cross-direction 255 stream into lanes which deposit onto the reinforcing material 202 forming the lanes of superabsorbent material 281*a-c*. As with the above description of FIG. 8, although the FIG. 9 depicts only two apertures 307, the mask member 301 may have any suitable number of apertures 307 to form the desired number of lanes of superabsorbent material in the reinforcing material 202.

In further embodiments where the superabsorbent material is deposited onto the reinforcing material 202 into lanes (such as lanes 281*a*-281*c*), the full core assembly 260 may be bonded, for example by rolls 261*a*, 261*b*, within at least some of the portions of the full core assembly 260 between the lanes of superabsorbent material. In this manner, superabsorbent material is not damaged during the bonding process. In some of these embodiments, the widths 283 between the lanes of superabsorbent material may vary. For example, the widths 283 may have an overall average width, and at least one individual width 283 may be larger than the overall average of the widths 283. Such portions of the full core assembly 260 between the lanes of superabsorbent material having widths 283 greater than the overall average of the widths 283 may have widths 283 which are greater than about 10% greater than the overall average of the widths 283, or greater than about 15%, or greater than about 20%, or greater than about 30% greater than the overall average of the widths 283. Such portions of the full core assembly 260 may have widths 283 which are less than about 75% or less than about 50% greater than the overall average of the widths 283.

The rolls 261*a*, 261*b* may be configured to bond the full core assembly 260 within such portions of the full core assembly 260 between the lanes 281*a*-281*c* having a width 283 greater than the average of the widths 283. In some embodiments, such portions of the full core assembly 260 are disposed at cross-direction side edges of the full core assembly 260 and form the end edges 137, 139 of the bodies 54 of the present disclosure. In such embodiments, the absorbent bodies 54 may have regions 147, 149 disposed proximate the end edges 137, 139, as shown with respect to FIGS. 3A and 4A (although, which are equally applicable to bodies 54 of FIGS. 3B, 4B, 5, and 6) which are substantially devoid of absorbent material. These regions 147, 149 may have widths that are less than about 15 mm, or less than about 10 mm, or less than about 5 mm. In further embodiments, such portions of the full core assembly 260 between the lanes 281*a*-281*c* and having a width 283 greater than the average of the widths 283 are spaced throughout the cross-direction dimension of the full core assembly 260. In such embodiments, the rolls 261*a*, 261*b* may bond the full core assembly 260 in at least some of these portions. The process 200 may then cut the full core assembly 260 through the bonded portions, forming distinct sections 267*a*-267*c*. Each of these distinct sections 267*a*-267*c* may then have bonded cross-direction edges which form the end edges 137, 139 of the bodies 54 of the present disclosure.

As described with respect to the method 200, superabsorbent material may be deposited onto the reinforcing material 202 on both the first side 206 and the second side 207. In some of these embodiments, the superabsorbent material may be deposited into lanes on both the first side 206 and the second side 207. For example, a mask member 301 may be associated with both of superabsorbent material hoppers 215 and 217 to distribute the dispensed superabsorbent material into lanes on both the first side 206 and the second side 207 of the reinforcing material 202.

Figure 10:
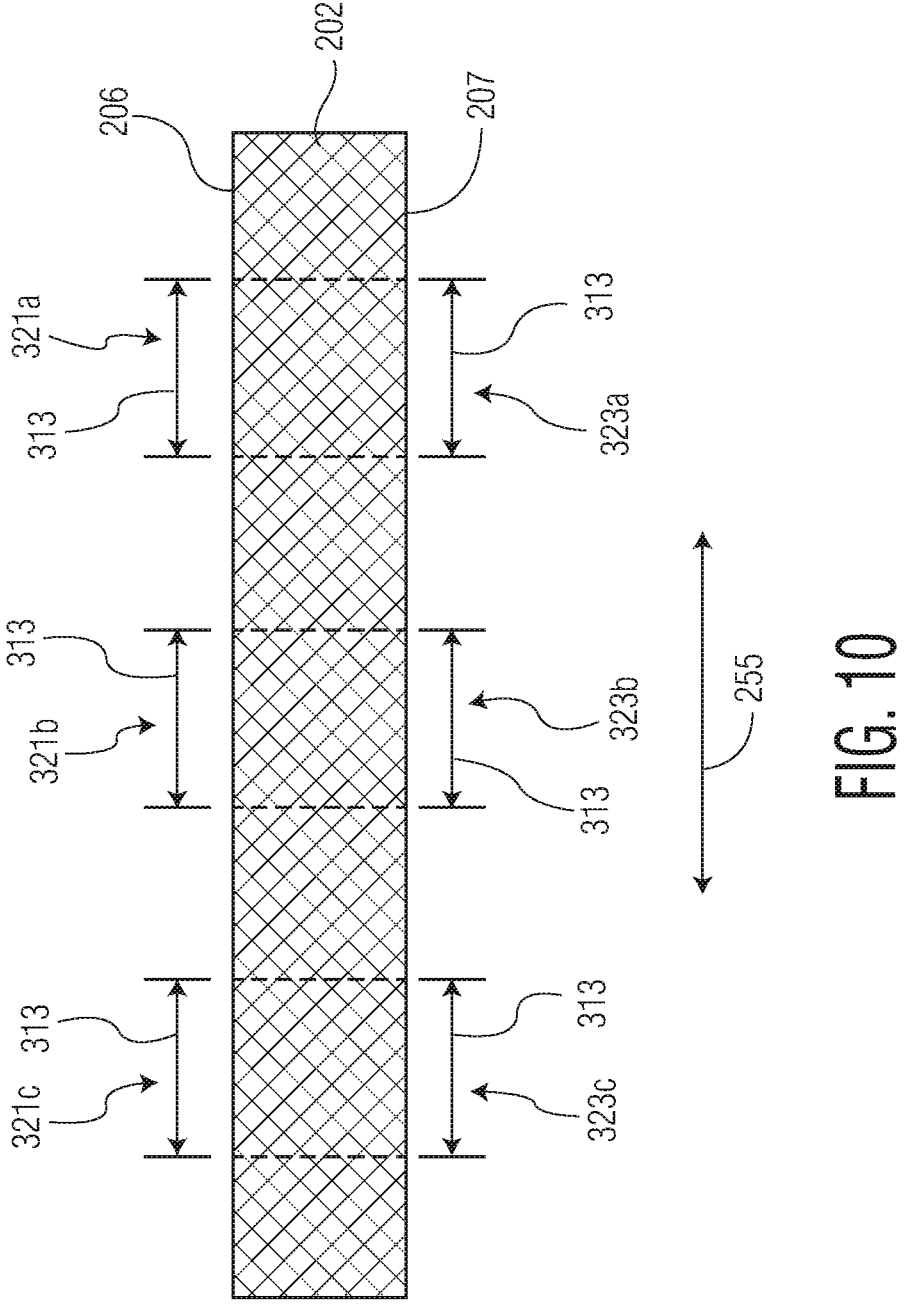
FIG. 10 is a cross-section view of a material used in the process depicted by FIGS. 6A and 6B showing particulate material deposition locations.

FIG. 10 is a cross-section of reinforcing material 202 depicting alignments, in the cross-direction 255, of the widths 313 of apertures associated with mask members, such as mask members 301, used in depositing of superabsorbent material onto both of the first side 206 and the second side 207 of the reinforcing material 202. As depicted in FIG. 10, the widths 313 associated with apertures of a mask member through which superabsorbent material is deposited onto the first side 206 of the reinforcing material 202 result in lanes of superabsorbent material 321*a*-321*c* (SAM particles not shown) while the widths 313 associated with apertures of a mask member through which superabsorbent material is deposited onto the second side 207 of the reinforcing material 202 result in lanes of superabsorbent material 323*a*-323*c* (SAM particles not shown). Of course, in some embodiments, the described widths 313 may also represent the widths of the lanes of superabsorbent material 321*a*-321*c*—for example where the deposited superabsorbent material does not appreciably spread in the cross-direction 255 beyond the bounds of the apertures 307. The alignments of lanes 321*a*-321*c* associated with the first side 206 of the reinforcing material 202 and the lanes 323*a*-323*c* associated with the second side 207 of the reinforcing material 202 may be such that the lanes 321*a*-321*c* and the lanes 323*a*-323*c* fully overlap in the cross-direction 255. Although each of the lanes 321*a*-321*c* are shown as fully overlapping the lanes 323*a*-323*c*, it should be understood that this is not required in all embodiments. Further embodiments may have only a portion of the lanes 321*a*-321*c* fully overlapping a portion of the lanes 323*a*-323*c*.

Figure 11:
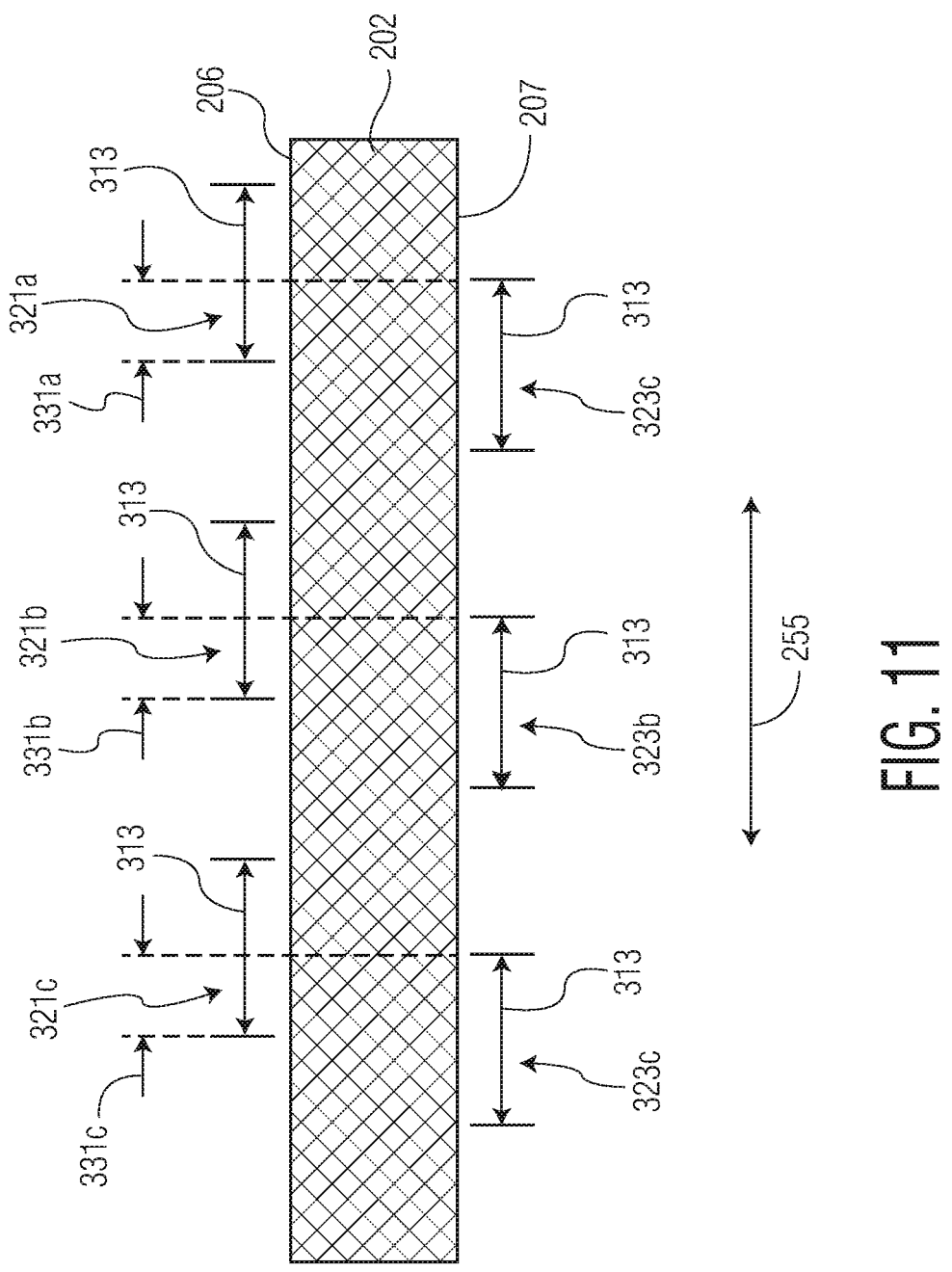
FIG. 11 is a cross-section view of a material used in the process depicted by FIGS. 6A and 6B showing alternate particulate material deposition locations.

FIG. 11 is a cross-section of reinforcing material 202 depicting further contemplated alignments, in the cross-direction 255, of the widths 313 of apertures associated with mask members, such as mask members 301, used in depositing superabsorbent material onto both of the first side 206 and the second side 207 of the reinforcing material 202. As depicted in FIG. 11, the widths 313 associated with apertures of a mask member through which superabsorbent material is deposited onto the first side 206 of the reinforcing material 202 result in lanes 321*a*-321*c* while the widths 313 associated with apertures of a mask member through which superabsorbent material is deposited onto the second side 207 of the reinforcing material 202 result in lanes 323*a*-323*c*. In the embodiment of FIG. 11, the lanes 321*a*-321*c* and the lanes 323*a*-323*c* only partially overlap in the cross-direction 255. As shown, the lanes 321*a*-321*c* and the lanes 323*a*-323*c* overlap for a distance 331*a*-331*c*, respectively, in the cross-direction 255. According to preferred embodiments, the overlap distances 331*a*-331*c* are between about 25% to about 75% of the width 313 of the lanes 321*a*-321*c*. In such embodiments, the width 313 of the apertures of the mask member used to form the lanes 321*a*-321*c* may be assumed to be the same as the actual width of the lanes 321*a*-321*c*. In further embodiments, the overlap distances 331*a*-331*c* are between about 33% to about 66% of the width 313 of the lanes 321*a*-321*c*.

In some of these embodiments, it may be the case that not every one of the lanes 321*a*-321*c* overlaps at least one of the lanes 323*a*-323*c*. To achieve a desired absorbent performance, it has been found that the combined overlapping widths in the cross-direction 255 of all of the lanes of the lanes 321*a*-321*c* which overlap any of the lanes 323*a*-323*c* should be between about 25% and about 75% of a total combined cross-direction width of the lanes 323*a*-323*c*. In further embodiments, it may be preferable for the combined overlapping widths in the cross-direction 255 of all of the lanes of the lanes 321*a*-321*c* which overlap any of the lanes 323*a*-323*c* to be between about 40% and about 60% of a total combined cross-direction width of the lanes 323*a*-323*c*

Figure 12:
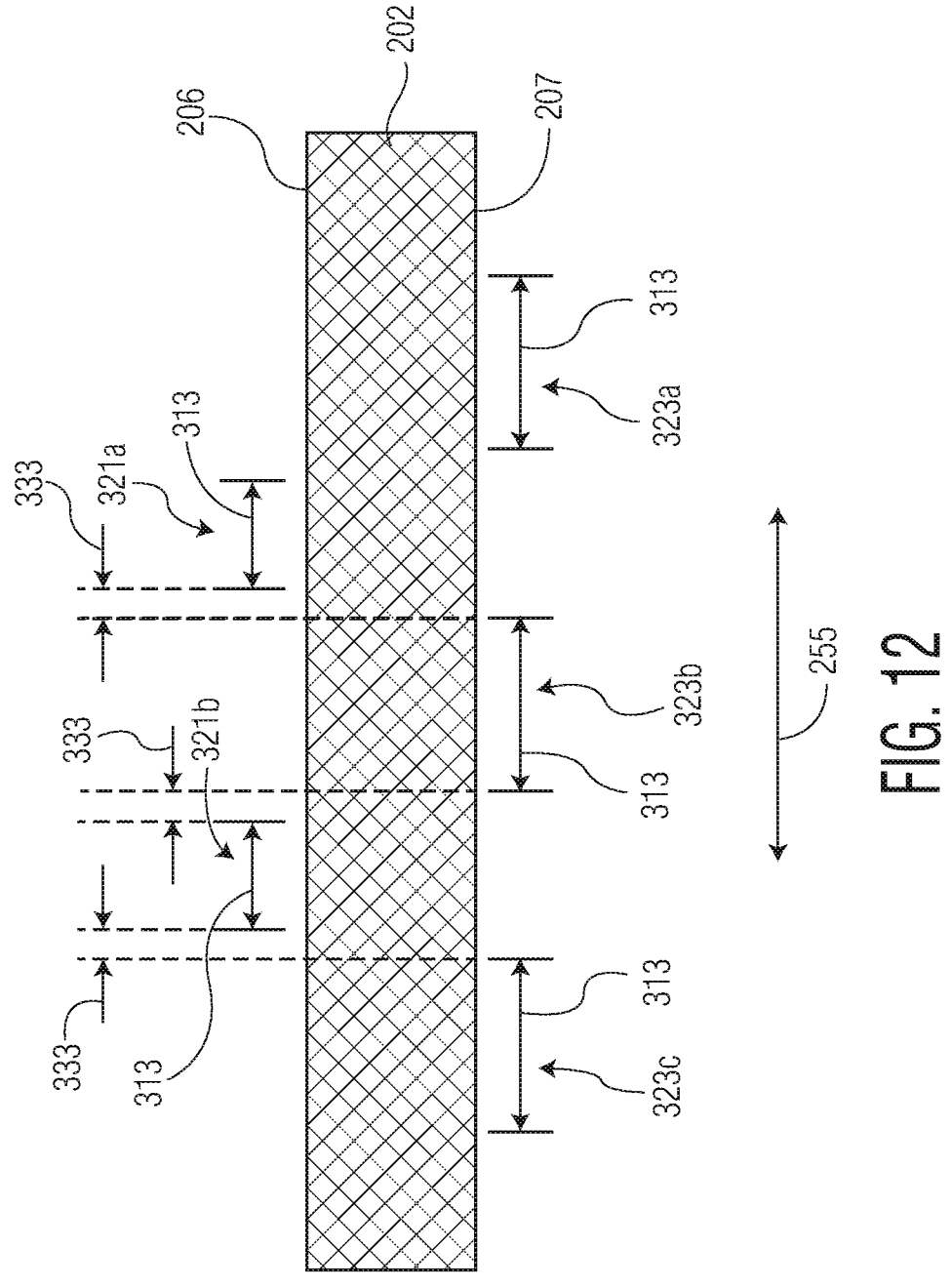
FIG. 12 is a cross-section view of a material used in the process depicted by FIGS. 6A and 6B showing further alternate particulate material deposition locations.

FIG. 12 is a cross-section of reinforcing material 202 depicting alignments, in the cross-direction 255, of the widths 313 of apertures associated with mask members, such as mask members 301, used in depositing superabsorbent material onto both of the first side 206 and the second side 207 of the reinforcing material 202. As depicted in FIG. 12, the widths 313 associated with apertures of a mask member through which superabsorbent material is deposited onto the first side 206 of the reinforcing material 202 result in lanes 321*a*-321*c* while the widths 313 associated with apertures of a mask member through which superabsorbent material is deposited onto the second side 207 of the reinforcing material 202 result in lanes 323*a*-323*c*. In the embodiment of FIG. 12, the lanes 321*a*-321*c* and the lanes 323*a*-323*c* do not overlap at all in the cross-direction 255. Rather, the lanes 321*a*-321*c* may be spaced from the lanes 323*a*-323*c* in the cross-direction by distances 333. In such embodiments, the width 313 of the apertures of the mask member used to form the lanes 321*a*-321*c* and lanes 323*a*-323*c* may be assumed to be the same as the actual width of the lanes 321*a*-321*c*, 323*a*-323*c*. According to preferred embodiments, the distances 333 may be between about 0 mm and about 25 mm. In further embodiments, the distances 333 may be between about 0 mm and about 20 mm, or between about 0 mm and about 15 mm, or between about 0 mm and about 10 mm.

While the invention has been described in detail with respect to the specific aspects thereof, it will be appreciated that those skilled in the art, upon attaining an understanding of the foregoing, may readily conceive of alterations to, variations of, and equivalents to these aspects.

EMBODIMENTS

Embodiment 1: An absorbent garment extending in a longitudinal and a lateral direction and comprising a bodyside liner, an outer cover, an absorbent body disposed between the bodyside liner and the outer cover, the absorbent body comprising: a top facing material layer, a bottom facing material layer, a lofty nonwoven reinforcing material disposed between the top facing material layer and the bottom facing material layer, absorbent material comprising superabsorbent material disposed between the top facing material layer and the bottom facing material layer and within the reinforcing material, and an acquisition material disposed between the absorbent body and the bodyside liner, and wherein a first side portion of the absorbent body and a second side portion of the absorbent body are folded onto a central portion of the absorbent body forming a folded absorbent body with a first folded portion and a second folded portion with a channel region disposed between the first folded portion and the second folded portion, and wherein the acquisition material spans across the channel region.

Embodiment 2: The absorbent garment of embodiment 1, wherein the channel region is disposed proximate the bodyside liner.

Embodiment 3: The absorbent garment of embodiment 1, wherein the channel region is disposed proximate the outer cover liner.

Embodiment 4: The absorbent garment of any one of embodiments 1-3, further comprising a first adhesive seam and a second adhesive seam, each of the first adhesive seam and the second adhesive seam bonding the top facing material layer to itself in each of the first folded portion and the second folded portion.

Embodiment 5: The absorbent garment of embodiment 4, wherein inboard edges of the first adhesive seam and the second adhesive seam are disposed at less than 5 mm from a first end edge and a second end edge, respectively, of the absorbent body.

Embodiment 6: The absorbent garment of any one of embodiment 4 and embodiment 5, wherein a width of each of the first adhesive seam and the second adhesive seam is less than 5 mm.

Embodiment 7: The absorbent garment of any one of embodiments 1-6, wherein the acquisition material is bonded to the bottom facing material layer.

Embodiment 8: The absorbent garment of any one of embodiments 1-7, wherein the acquisition material is bonded into the channel region.

Embodiment 9: The absorbent garment of any one of embodiments 1-8, wherein the acquisition material is bonded to the top facing material layer in the channel region.

Embodiment 10: The absorbent garment of any one of embodiments 1-8, wherein the acquisition material is bonded to the absorbent body by a first lateral adhesive zone and a second lateral adhesive zone, wherein an adhesive-free zone is disposed between the first lateral adhesive zone and the second lateral adhesive zone, the adhesive-free zone overlapping the channel region.

Embodiment 11: The absorbent garment of any one of embodiments 1-8 and 10, wherein the acquisition material is unbonded to the top facing material layer.

Embodiment 12: The absorbent garment of any one of embodiments 1-11, wherein the folded absorbent body has a lateral width, the channel region has a lateral width, and the channel region lateral width being between 30% and 70% of the folded absorbent body lateral width.

Embodiment 13: The absorbent garment of any one of embodiments 1-12, wherein the folded absorbent body has a lateral width, the channel region has a lateral width, and the channel region lateral width being between 40% and 60% of the folded absorbent body lateral width.

Embodiment 14: The absorbent garment of any one of embodiments 1-13, wherein the superabsorbent material is deposited onto the reinforcing material on both a first side of the reinforcing material and a second side of the reinforcing material.

Embodiment 15: The absorbent garment of any one of embodiments 1-14, wherein the superabsorbent material is deposited onto the first side of the reinforcing material to form superabsorbent material lane regions on the first side of the reinforcing material and onto the second side of the reinforcing material to form superabsorbent material lane regions on the second side of the reinforcing material, the superabsorbent material lane regions on the first side of the reinforcing material being spaced apart other and the superabsorbent material lane regions on the second side of the reinforcing material being spaced apart.

Embodiment 16: The absorbent garment of embodiment 15, wherein the superabsorbent material lane regions on the first side of the reinforcing material laterally overlap with superabsorbent material lane regions on the second side of the reinforcing material.

Embodiment 17: The absorbent garment of any one of embodiment 15 and embodiment 16, wherein the superabsorbent material lane regions on the first side of the reinforcing material have widths in the lateral direction, and wherein a total combined overlapping width of all of the lateral widths for which the superabsorbent material lane regions on the first side of the reinforcing material laterally overlap with superabsorbent material lane regions on the second side of the reinforcing material is greater than 50% of a total combined width of superabsorbent material lane regions on the first side of the reinforcing material.

Embodiment 18: The absorbent garment of any one of embodiments 15-17, wherein the superabsorbent material lane regions on the first side of the reinforcing material have widths in the lateral direction, and wherein a total combined overlapping width of all of the lateral widths for which the superabsorbent material lane regions on the first side of the reinforcing material laterally overlap with superabsorbent material lane regions on the second side of the reinforcing material is greater than 75% of a total combined width of superabsorbent material lane regions on the first side of the reinforcing material.

Embodiment 19: The absorbent garment of embodiment 15, wherein none of the superabsorbent material lane regions on the first side of the reinforcing material laterally overlap with superabsorbent material lane regions on the second side of the reinforcing material.

Embodiment 20: The absorbent garment of any one of embodiments 15-19, wherein the superabsorbent material lane regions on the first side of the reinforcing material have first lateral widths, the superabsorbent material lane regions on the second side of the reinforcing material have second lateral widths, and wherein the first lateral widths and the second lateral widths are between 3 mm and 20 mm.

Embodiment 21: The absorbent garment of embodiment 20, wherein the first lateral widths and the second lateral widths are between 5 mm and 15 mm.

Embodiment 22: The absorbent garment of embodiment 20, wherein the first lateral widths and the second lateral widths are between 5 mm and 10 mm.

Embodiment 23: The absorbent garment of any one of embodiments 15-22, wherein a combined width of the superabsorbent material lanes comprises between 40% and 60% of an overall width of the folded absorbent body.

Embodiment 24: The absorbent garment of any one of embodiments 15-23, wherein the superabsorbent material lane regions on the first side of the reinforcing material are spaced apart by a first set of widths, the superabsorbent material lane regions on the second side of the reinforcing material are spaced by a second set of widths, wherein a difference between a smallest of the first set of widths and a largest of the first set of widths is less than 250% of the smallest of the first set of widths, and wherein a difference between a smallest of the second set of widths and a largest of the second set of widths is less than 250% of the smallest of the second set of widths.

Embodiment 25: The absorbent garment of any one of embodiments 15-23, wherein the superabsorbent material lane regions on the first side of the reinforcing material are spaced apart by a first set of widths, the superabsorbent material lane regions on the second side of the reinforcing material are spaced by a second set of widths, wherein a difference between a smallest of the first set of widths and a largest of the first set of widths is less than 150% of the smallest of the first set of widths, and wherein a difference between a smallest of the second set of widths and a largest of the second set of widths is less than 150% of the smallest of the second set of widths.

Embodiment 26: The absorbent garment of any one of embodiments 15-25, wherein regions disposed between the superabsorbent material lane regions on the first side of the reinforcing material and the superabsorbent material lane regions on the second side of the reinforcing material are substantially devoid of absorbent material disposed between the lanes of superabsorbent material.

Embodiment 27: The absorbent garment of any one of embodiments 15-26, wherein the absorbent body has a first height as measured at a location containing a superabsorbent material lane region and has a second height as measured at a location between superabsorbent material lane regions, and wherein the first height is between 20% and 80% greater than the second height.

Embodiment 28: The absorbent garment of any one of embodiments 15-26, wherein the absorbent body has a first height as measured at a location containing a superabsorbent material lane region and has a second height as measured at a location between superabsorbent material lane regions, and wherein the first heigh is between 35% and 65% greater than the second height.

Embodiment 29: The absorbent garment of any one of embodiments 15-28, wherein a first superabsorbent material lane region disposed within a first side portion of the absorbent body fully overlaps a superabsorbent material lane region in a central portion of the absorbent body within a first folded portion and a second superabsorbent material lane region disposed within a second side portion of the absorbent body fully overlaps a superabsorbent material lane region in the central portion of the absorbent body within a second folded portion of the absorbent body.

Embodiment 30: The absorbent garment of any one of embodiments 15-28, wherein a first superabsorbent material lane region disposed within a first side portion of the absorbent body overlaps a superabsorbent material lane region in a central portion of the absorbent body within a first folded portion for an overlap width of between 25% and 75% of a width of the first superabsorbent material lane region, and wherein a second superabsorbent material lane region disposed within a second side portion of the absorbent body overlaps a superabsorbent material lane region in the central portion of the absorbent body within a second folded portion for an overlap width of between 25% and 75% of a width of the second superabsorbent material lane region.

Embodiment 31: The absorbent garment of any one of embodiments 1-30, wherein end edges of the absorbent body, include the top facing material layer, the bottom facing material layer, and the reinforcing material are bonded together by heat, pressure, and/or ultrasonic energy.

Embodiment 32: The absorbent garment of any one of embodiments 1-31, wherein the absorbent body is substantially devoid of absorbent material within 10 mm of end edges of the absorbent body.

Embodiment 33: The absorbent garment of any one of embodiments 1-31, wherein the absorbent body is substantially devoid of absorbent material within 5 mm of end edges of the absorbent body Embodiment 34: The absorbent garment of any one of embodiments 1-33, further including an integrity sheet disposed between the absorbent body and the outer cover, the integrity sheet comprising a coform material, a TABCW material, or a spunlace material.

Embodiment 35: The absorbent garment of any one of embodiments 1-34, wherein the top facing material comprises a tissue material, a spunbond material, or a spunlace material.

Embodiment 36: The absorbent garment of any one of embodiments 1-35, wherein the bottom facing material comprises a coform material, a spunbond material, or a spunlace material.

Embodiment 37: The absorbent garment of any one of embodiments 1-36, wherein the reinforcing material comprises a spunlace material or a TABCW material.

Embodiment 38: An absorbent garment extending in a longitudinal and a lateral direction and comprising a bodyside liner, an outer cover, an absorbent body disposed between the bodyside liner and the outer cover, the absorbent body comprising: a top facing material layer, a bottom facing material layer, a lofty nonwoven reinforcing material disposed between the top facing material layer and the bottom facing material layer, absorbent material comprising superabsorbent material disposed between the top facing material layer and the bottom facing material layer and within the reinforcing material, and an acquisition material disposed between the absorbent body and the bodyside liner, wherein the superabsorbent material is deposited onto the first side of the reinforcing material to form superabsorbent material lane regions on the first side of the reinforcing material and onto the second side of the reinforcing material to form superabsorbent material lane regions on the second side of the reinforcing material, the superabsorbent material lane regions on the first side of the reinforcing material being spaced from apart and the superabsorbent material lane regions on the second side of the reinforcing material being spaced apart and wherein a combined width of the superabsorbent material lanes comprises between 40% and 60% of an overall width of the folded absorbent body.

Embodiment 39: The absorbent garment of embodiment 38, wherein the superabsorbent material lane regions on the first side of the reinforcing material laterally overlap with superabsorbent material lane regions on the second side of the reinforcing material.

Embodiment 40: The absorbent garment of any one of embodiment 38 and embodiment 39, wherein the superabsorbent material lane regions on the first side of the reinforcing material have widths in the lateral direction, and wherein a total combined overlapping width of all of the lateral widths for which the superabsorbent material lane regions on the first side of the reinforcing material laterally overlap with superabsorbent material lane regions on the second side of the reinforcing material is greater than 50% % of a total combined width of superabsorbent material lane regions on the first side of the reinforcing material.

Embodiment 41: The absorbent garment of any one of embodiments 38-40, wherein the superabsorbent material lane regions on the first side of the reinforcing material have widths in the lateral direction, and wherein a total combined overlapping width of all of the lateral widths for which the superabsorbent material lane regions on the first side of the reinforcing material laterally overlap with superabsorbent material lane regions on the second side of the reinforcing material is greater than 75% of a total combined width of superabsorbent material lane regions on the first side of the reinforcing material.

Embodiment 42: The absorbent garment of any one of embodiments 38-41, wherein none of the superabsorbent material lane regions on the first side of the reinforcing material laterally overlap with superabsorbent material lane regions on the second side of the reinforcing material.

Embodiment 43: The absorbent garment of any one of embodiments 38-42, wherein the superabsorbent material lane regions on the first side of the reinforcing material have first lateral widths, the superabsorbent material lane regions on the second side of the reinforcing material have second lateral widths, and wherein the first lateral widths and the second lateral widths are between 3 mm and 20 mm.

Embodiment 44: The absorbent garment of embodiment 43, wherein the first lateral widths and the second lateral widths are between 5 mm and 15 mm.

Embodiment 45: The absorbent garment of embodiment 433, wherein the first lateral widths and the second lateral widths are between 5 mm and 10 mm.

Embodiment 46: The absorbent garment of any one of embodiments 38-45, wherein the superabsorbent material lane regions on the first side of the reinforcing material are spaced apart by a first set of widths, the superabsorbent material lane regions on the second side of the reinforcing material are spaced by a second set of widths, wherein a difference between a smallest of the first set of widths and a largest of the first set of widths is less than 250% of the smallest of the first set of widths, and wherein a difference between a smallest of the second set of widths and a largest of the second set of widths is less than 250% of the smallest of the second set of widths.

Embodiment 47: The absorbent garment of any one of embodiments 38-46, wherein the superabsorbent material lane regions on the first side of the reinforcing material are spaced apart by a first set of widths, the superabsorbent material lane regions on the second side of the reinforcing material are spaced by a second set of widths, wherein a difference between a smallest of the first set of widths and a largest of the first set of widths is less than 150% of the smallest of the first set of widths, and wherein a difference between a smallest of the second set of widths and a largest of the second set of widths is less than 150% of the smallest of the second set of widths.

Embodiment 48: The absorbent garment of any one of embodiments 38-47, wherein regions disposed between the superabsorbent material lane regions on the first side of the reinforcing material and the superabsorbent material lane regions on the second side of the reinforcing material are substantially devoid of absorbent material disposed between the lanes of superabsorbent material.

Embodiment 49: The absorbent garment of any one of embodiments 38-48, wherein the absorbent body has a first height as measured at a location containing a superabsorbent material lane region and has a second height as measured at a location between superabsorbent material lane regions, and wherein the first height is between 20% and 80% greater than the second height.

Embodiment 50: The absorbent garment of any one of embodiments 38-48, wherein the absorbent body has a first height as measured at a location containing a superabsorbent material lane region and has a second height as measured at a location between superabsorbent material lane regions, and wherein the first heigh is between 35% and 65% greater than the second height.

Embodiment 51: The absorbent garment of any one of embodiments 38-50, wherein end edges of the absorbent body, include the top facing material layer, the bottom facing material layer, and the reinforcing material are bonded together by heat, pressure, and/or ultrasonic energy.

Embodiment 52: The absorbent garment of any one of embodiments 38-51, wherein the absorbent body is substantially devoid of absorbent material within 10 mm of end edges of the absorbent body.

Embodiment 53: The absorbent garment of any one of embodiments 38-52, wherein the absorbent body is substantially devoid of absorbent material within 5 mm of end edges of the absorbent body Embodiment 54: The absorbent garment of any one of embodiments 38-53, further including an integrity sheet disposed between the absorbent body and the outer cover, the integrity sheet comprising a coform material, a TABCW material, or a spunlace material.

Embodiment 55: The absorbent garment of any one of embodiments 38-54, wherein the top facing material comprises a tissue material, a spunbond material, or a spunlace material.

Embodiment 56: The absorbent garment of any one of embodiments 38-55, wherein the bottom facing material comprises a coform material, a spunbond material, or a spunlace material.

Embodiment 57: The absorbent garment of any one of embodiments 38-56, wherein the reinforcing material comprises a spunlace material or a TABCW material.

Embodiment 58: An absorbent garment extending in a longitudinal and a lateral direction and comprising a bodyside liner, an outer cover, an absorbent body disposed between the bodyside liner and the outer cover, the absorbent body comprising: a top facing material layer, a bottom facing material layer, a lofty nonwoven reinforcing material disposed between the top facing material layer and the bottom facing material layer, absorbent material comprising superabsorbent material forming a plurality of spaced superabsorbent material lanes disposed between the top facing material layer and the bottom facing material layer and within the reinforcing material, wherein a first side portion of the absorbent body and a second side portion of the absorbent body are folded onto a central portion of the absorbent body forming a folded absorbent body with a first folded portion and a second folded portion with a channel region disposed between the first folded portion and the second folded portion, and wherein the superabsorbent material lanes spaced apart by a of distance between 5 mm and 15 mm and a combined width of the superabsorbent material lanes comprises between 40% and 60% of an overall width of the folded absorbent body; and an acquisition material disposed between the absorbent body and the bodyside liner, wherein the acquisition material spans across the channel region and is bonded into the channel.

Embodiment 59: The absorbent garment of embodiment 58, further comprising a first adhesive seam and a second adhesive seam, each of the first adhesive seam and the second adhesive seam bonding the top facing material layer to itself in each of the first folded portion and the second folded portion.

Embodiment 60: The absorbent garment of embodiment 59, wherein inboard edges of the first adhesive seam and the second adhesive seam are disposed at less than 5 mm from a first end edge and a second end edge, respectively, of the absorbent body.

Embodiment 61: The absorbent garment of any one of embodiment 59 and embodiment 60, wherein a width of each of the first adhesive seam and the second adhesive seam is less than 5 mm.

Embodiment 62: The absorbent garment of any one of embodiments 58-61, wherein the acquisition material is bonded to the bottom facing material layer.

Embodiment 61: The absorbent garment of any one of embodiments 58-62, wherein the acquisition material is bonded to the top facing material layer in the channel region.

Embodiment 62: The absorbent garment of any one of embodiments 58-61, wherein the folded absorbent body has a lateral width, the channel region has a lateral width, and the channel region lateral width being between 30% and 70% of the folded absorbent body lateral width.

Embodiment 63: The absorbent garment of any one of embodiments 58-61, wherein the folded absorbent body has a lateral width, the channel region has a lateral width, and the channel region lateral width being between 40% and 60% of the folded absorbent body lateral width.

Embodiment 64: The absorbent garment of any one of embodiments 58-63, wherein the superabsorbent material is deposited onto the reinforcing material on both a first side of the reinforcing material and a second side of the reinforcing material.

Embodiment 65: The absorbent garment of any one of embodiments 58-63, wherein the superabsorbent material is deposited onto the first side of the reinforcing material to form superabsorbent material lane regions on the first side of the reinforcing material and onto the second side of the reinforcing material to form superabsorbent material lane regions on the second side of the reinforcing material, the superabsorbent material lane regions on the first side of the reinforcing material being spaced apart and the superabsorbent material lane regions on the second side of the reinforcing material being spaced apart.

Embodiment 66: The absorbent garment of embodiment 65, wherein the superabsorbent material lane regions on the first side of the reinforcing material laterally overlap with superabsorbent material lane regions on the second side of the reinforcing material.

Embodiment 67: The absorbent garment of any one of embodiment 65 and embodiment 66, wherein the superabsorbent material lane regions on the first side of the reinforcing material have widths in the lateral direction, and wherein a total combined overlapping width of all of the lateral widths for which the superabsorbent material lane regions on the first side of the reinforcing material laterally overlap with superabsorbent material lane regions on the second side of the reinforcing material is greater than 50% of a total combined width of superabsorbent material lane regions on the first side of the reinforcing material.

Embodiment 68: The absorbent garment of any one of embodiments 65-67, wherein the superabsorbent material lane regions on the first side of the reinforcing material have widths in the lateral direction, and wherein a total combined overlapping width of all of the lateral widths for which the superabsorbent material lane regions on the first side of the reinforcing material laterally overlap with superabsorbent material lane regions on the second side of the reinforcing material is greater than 75% of a total combined width of superabsorbent material lane regions on the first side of the reinforcing material.

Embodiment 69: The absorbent garment of any one of embodiments 65-68, wherein the superabsorbent material lane regions on the first side of the reinforcing material are spaced apart by a first set of widths, the superabsorbent material lane regions on the second side of the reinforcing material are spaced by a second set of widths, wherein a difference between a smallest of the first set of widths and a largest of the first set of widths is less than 250% of the smallest of the first set of widths, and wherein a difference between a smallest of the second set of widths and a largest of the second set of widths is less than 250% of the smallest of the second set of widths.

Embodiment 70: The absorbent garment of any one of embodiments 65-68, wherein the superabsorbent material lane regions on the first side of the reinforcing material are spaced apart by a first set of widths, the superabsorbent material lane regions on the second side of the reinforcing material are spaced by a second set of widths, wherein a difference between a smallest of the first set of widths and a largest of the first set of widths is less than 150% of the smallest of the first set of widths, and wherein a difference between a smallest of the second set of widths and a largest of the second set of widths is less than 150% of the smallest of the second set of widths.

Embodiment 71: The absorbent garment of any one of embodiments 65-70, wherein regions disposed between the superabsorbent material lane regions on the first side of the reinforcing material and the superabsorbent material lane regions on the second side of the reinforcing material are substantially devoid of absorbent material disposed between the lanes of superabsorbent material.

Embodiment 72: The absorbent garment of any one of embodiments 65-71, wherein the absorbent body has a first height as measured at a location containing a superabsorbent material lane region and has a second height as measured at a location between superabsorbent material lane regions, and wherein the first height is between 20% and 80% greater than the second height.

Embodiment 73: The absorbent garment of any one of embodiments 65-71, wherein the absorbent body has a first height as measured at a location containing a superabsorbent material lane region and has a second height as measured at a location between superabsorbent material lane regions, and wherein the first heigh is between 35% and 65% greater than the second height.

Embodiment 74: The absorbent garment of any one of embodiments 65-73, wherein a first superabsorbent material lane region disposed within a first side portion of the absorbent body fully overlaps a superabsorbent material lane region in a central portion of the absorbent body within a first folded portion and a second superabsorbent material lane region disposed within a second side portion of the absorbent body fully overlaps a superabsorbent material lane region in the central portion of the absorbent body within a second folded portion of the absorbent body.

Embodiment 75: The absorbent garment of any one of embodiments 65-73, wherein a first superabsorbent material lane region disposed within a first side portion of the absorbent body overlaps a superabsorbent material lane region in a central portion of the absorbent body within a first folded portion for an overlap width of between 25% and 75% of a width of the first superabsorbent material lane region, and wherein a second superabsorbent material lane region disposed within a second side portion of the absorbent body overlaps a superabsorbent material lane region in the central portion of the absorbent body within a second folded portion for an overlap width of between 25% and 75% of a width of the second superabsorbent material lane region.

Embodiment 76: A method of forming an absorbent garment, the method comprising: moving a first facing material in a machine direction, moving a reinforcing material in the machine direction, the reinforcing material having a first side and a second side, applying superabsorbent material to the first side of the reinforcing material, the first side of the reinforcing material facing up in a vertical direction, reversing an orientation of the reinforcing material so that the first side of the reinforcing material faces down in the vertical direction, applying the first side of the reinforcing material to the first facing material, applying superabsorbent material to the second side of the reinforcing material, moving a second facing material in the machine direction, applying the second facing material to the second side of the reinforcing material to form an absorbent laminate comprising the first facing material, the reinforcing material, and the second facing material, folding a first side portion and a second side portion of the absorbent laminate onto a central portion of the absorbent laminate, the first side portion and the second side portion folded onto the central portion to form a channel region in the folded absorbent laminate, moving an acquisition material in the machine direction, coupling the acquisition material to the folded absorbent laminate such that the acquisition material spans across the channel region, and coupling the folded absorbent laminate and the acquisition material between a bodyside liner material and an outer cover material to form an absorbent garment.

Embodiment 77: The method of embodiment 76, further comprising bonding the absorbent laminate with heat, pressure, and/or ultrasonic energy to form end edges of the absorbent laminate.

Embodiment 78: The method of embodiment 76, wherein applying superabsorbent material to the first side of the reinforcing material and the second side of the reinforcing material comprises applying superabsorbent material to the first side and the second side of the reinforcing material in spaced apart superabsorbent material lane regions spaced.

Embodiment 79: The method of embodiment 78, wherein regions between the superabsorbent material lane regions are substantially devoid of superabsorbent material.

Embodiment 80: The method of any one of embodiment 78 and embodiment 79, further comprising bonding the absorbent laminate with heat, pressure, and/or ultrasonic energy within the regions between the superabsorbent material lane regions.

Embodiment 81: The method of any one of embodiments 78-80, further comprising cutting the absorbent laminate in the spaces between the superabsorbent material lane regions.

Embodiment 82: The method of embodiment 81, further comprising cutting the absorbent laminate in the spaces between the superabsorbent material lane regions to form a plurality of streams of the absorbent laminate, and a first side portion and a second side portion of each of the plurality of streams of the absorbent laminate are folded onto a central portion to form a channel region.

Embodiment 83: The method of any one of embodiments 76-81, further complying applying a seam adhesive to a first side portion of the absorbent laminate or plurality of streams of absorbent laminate and to a second side portion of the absorbent laminate or each of the plurality of streams of absorbent laminate prior to folding the absorbent laminate or plurality of streams of absorbent laminate.

Embodiment 84: The method of embodiment 83, wherein a width of each of the adhesive seam applied to the first side portion and the second side portion of the absorbent laminate or each of the plurality of streams of absorbent laminate is less than 5 mm.

Embodiment 85: The method of any one of embodiments 76-84, wherein the acquisition material is coupled to the first facing material layer.

Embodiment 86: The method of any one of embodiments 76-85, wherein the acquisition material is coupled to the second facing material in the channel region.

Embodiment 87: The method of any one of embodiments 76-85, wherein the acquisition material is coupled to the folded absorbent laminate by a first lateral adhesive zone and a second lateral adhesive zone, wherein an adhesive-free zone is disposed between the first lateral adhesive zone and the second lateral adhesive zone, the adhesive-free zone overlapping the channel region.

Embodiment 88: The method of any one of embodiments 76-87, wherein the folded absorbent laminate has a lateral width, the channel region has a lateral width, and the channel region lateral width being between 30% and 70% of the folded absorbent body lateral width.

Embodiment 89: The method of any one of embodiments 76-87, wherein the folded absorbent laminate has a lateral width, the channel region has a lateral width, and the channel region lateral width being between 40% and 60% of the folded absorbent body lateral width.

Embodiment 90: The method of any one of embodiments 78-89, wherein the superabsorbent material lane regions on the first side of the reinforcing material laterally overlap with superabsorbent material lane regions on the second side of the reinforcing material.

Embodiment 91: The method of any one of embodiment 78 and embodiment 90, wherein the superabsorbent material lane regions on the first side of the reinforcing material have widths in the lateral direction, and wherein a total combined overlapping width of all of the lateral widths for which the superabsorbent material lane regions on the first side of the reinforcing material laterally overlap with superabsorbent material lane regions on the second side of the reinforcing material is greater than 50% of a total combined width of superabsorbent material lane regions on the first side of the reinforcing material.

Embodiment 92: The method of any one of embodiment 78 and embodiment 90, wherein the superabsorbent material lane regions on the first side of the reinforcing material have widths in the lateral direction, and wherein a total combined overlapping width of all of the lateral widths for which the superabsorbent material lane regions on the first side of the reinforcing material laterally overlap with superabsorbent material lane regions on the second side of the reinforcing material is greater than 75% of a total combined width of superabsorbent material lane regions on the first side of the reinforcing material.

Embodiment 93: The method of any one of embodiments 77 and 90-92, wherein the superabsorbent material lane regions on the first side of the reinforcing material have first lateral widths, the superabsorbent material lane regions on the second side of the reinforcing material have second lateral widths, and wherein the first lateral widths and the second lateral widths are between 3 mm and 20 mm.

Embodiment 94: The method of embodiment 93, wherein the first lateral widths and the second lateral widths are between 5 mm and 15 mm.

Embodiment 95: The method of embodiment 93, wherein the first lateral widths and the second lateral widths are between 5 mm and 10 mm.

Embodiment 96: The method of any one of embodiments 77 and 90-95, wherein a combined width of the superabsorbent material lanes comprises between 40% and 60% of an overall width of the folded absorbent body.

Embodiment 97: The method of any one of embodiments 77 and 90-96, wherein the superabsorbent material lane regions on the first side of the reinforcing material are spaced apart by a first set of widths, the superabsorbent material lane regions on the second side of the reinforcing material are spaced by a second set of widths, wherein a difference between a smallest of the first set of widths and a largest of the first set of widths is less than 250% of the smallest of the first set of widths, and wherein a difference between a smallest of the second set of widths and a largest of the second set of widths is less than 250% of the smallest of the second set of widths.

Embodiment 98: The method of any one of embodiments 77 and 90-96, wherein the superabsorbent material lane regions on the first side of the reinforcing material are spaced apart by a first set of widths, the superabsorbent material lane regions on the second side of the reinforcing material are spaced by a second set of widths, wherein a difference between a smallest of the first set of widths and a largest of the first set of widths is less than 150% of the smallest of the first set of widths, and wherein a difference between a smallest of the second set of widths and a largest of the second set of widths is less than 150% of the smallest of the second set of widths.

Embodiment 99: The method of any one of embodiments 77 and 90-98, wherein the absorbent body has a first height as measured at a location containing a superabsorbent material lane region and has a second height as measured at a location between superabsorbent material lane regions, and wherein the first height is between 20% and 80% greater than the second height.

Embodiment 100: The method of any one of embodiments 77 and 90-98, wherein the absorbent body has a first height as measured at a location containing a superabsorbent material lane region and has a second height as measured at a location between superabsorbent material lane regions, and wherein the first heigh is between 35% and 65% greater than the second height.

Embodiment 101: The method of any one of embodiments 77 and 90-100, wherein a first superabsorbent material lane region disposed within a first side portion of the absorbent body fully overlaps a superabsorbent material lane region in a central portion of the absorbent body within a first folded portion and a second superabsorbent material lane region disposed within a second side portion of the absorbent body fully overlaps a superabsorbent material lane region in the central portion of the absorbent body within a second folded portion of the absorbent body.

Embodiment 102: The method of any one of embodiments 77 and 90-101, wherein a first superabsorbent material lane region disposed within a first side portion of the absorbent body overlaps a superabsorbent material lane region in a central portion of the absorbent body within a first folded portion for an overlap width of between 25% and 75% of a width of the first superabsorbent material lane region, and wherein a second superabsorbent material lane region disposed within a second side portion of the absorbent body overlaps a superabsorbent material lane region in the central portion of the absorbent body within a second folded portion for an overlap width of between 25% and 75% of a width of the second superabsorbent material lane region.

We claim:

1. An absorbent garment extending in a longitudinal and a lateral direction and comprising:
   a bodyside liner;
   an outer cover;
      an absorbent body disposed between the bodyside liner and the outer cover, the absorbent body comprising:
      a top facing material layer,
      a bottom facing material layer,
         a lofty nonwoven reinforcing material disposed between the top facing material layer and the bottom facing material layer the lofty nonwoven reinforcing material being a through-air bonded carded web (TABCW) material having a basis weight of between 15 gsm and about 60 gsm and made of polyolefin fibers,
         absorbent material comprising superabsorbent material disposed between the top facing material layer and the bottom facing material layer and within the reinforcing material, the superabsorbent material being disposed in a plurality of spaced superabsorbent material lanes forming discrete first regions containing superabsorbent material and second regions being devoid of superabsorbent material, and
      an acquisition material disposed between the absorbent body and the bodyside liner,
      wherein a first side portion of the absorbent body and a second side portion of the absorbent body are folded onto a central portion of the absorbent body forming a folded absorbent body with a first folded portion and a second folded portion with a channel region disposed between the first folded portion and the second folded portion, and wherein the acquisition material spans across the channel region,
      wherein at least one first region containing superabsorbent material and at least one second region being devoid of superabsorbent material are present in each of the first folded portion and the second folded portion.

2. The absorbent garment of claim 1, wherein the channel region is disposed proximate the bodyside liner.

3. The absorbent garment of claim 1, further comprising a first adhesive seam and a second adhesive seam, each of the first adhesive seam and the second adhesive seam bonding the top facing material layer to itself in each of the first folded portion and the second folded portion.

4. The absorbent garment of claim 1, wherein the acquisition material is bonded to the top facing material layer in the channel region.

5. The absorbent garment of claim 1, wherein the acquisition material is bonded to the absorbent body by a first lateral adhesive zone and a second lateral adhesive zone, wherein an adhesive-free zone is disposed between the first lateral adhesive zone and the second lateral adhesive zone, the adhesive-free zone overlapping the channel region.

6. The absorbent garment of claim 1, wherein the folded absorbent body has a lateral width, the channel region has a lateral width, and the channel region lateral width being between 40% and 60% of the folded absorbent body lateral width.

7. The absorbent garment of claim 1, wherein the superabsorbent material is deposited onto the reinforcing material on both a first side of the reinforcing material and a second side of the reinforcing material.

8. The absorbent garment of claim 7, wherein the superabsorbent material is deposited onto the first side of the reinforcing material such that it forms a plurality of spaced superabsorbent material lanes on the first side of the reinforcing material and onto the second side of the reinforcing material such that it forms a plurality of spaced superabsorbent material lanes on the second side of the reinforcing material.

9. The absorbent garment of claim 8, wherein the plurality of superabsorbent material lanes on the first side of the reinforcing material laterally overlap with the plurality of spaced superabsorbent material lanes on the second side of the reinforcing material.

10. The absorbent garment of claim 9, wherein the plurality of spaced superabsorbent material lanes on the first side of the reinforcing material have widths in the lateral direction, and wherein a total combined overlapping width of all of the lateral widths for which the plurality of spaced superabsorbent material lanes on the first side of the reinforcing material laterally overlap with the plurality of spaced superabsorbent material lanes on the second side of the reinforcing material is greater than 50% of a total combined width of the plurality of spaced superabsorbent material on the first side of the reinforcing material.

11. The absorbent garment of claim 8, wherein the plurality of spaced superabsorbent material lanes on the first side of the reinforcing material are spaced apart by a first set of widths, the plurality of spaced superabsorbent material lanes on the second side of the reinforcing material are spaced by a second set of widths, wherein a difference between a smallest of the first set of widths and a largest of the first set of widths is less than 150% of the smallest of the first set of widths, and wherein a difference between a smallest of the second set of widths and a largest of the second set of widths is less than 150% of the smallest of the second set of widths.

12. The absorbent garment of claim 8, wherein the absorbent body has a first height as measured at a location containing a superabsorbent material lane and has a second height as measured at a location between superabsorbent material lanes, and wherein the first height is between 20% and 80% greater than the second height.

13. The absorbent garment of claim 1, wherein the absorbent body is substantially devoid of absorbent material within 10 mm of end edges of the absorbent body.

14. An absorbent garment extending in a longitudinal and a lateral direction and comprising:
   a bodyside liner;
   an outer cover;
   an absorbent body disposed between the bodyside liner and the outer cover, the absorbent body comprising:
   a top facing material layer,
   a bottom facing material layer,
      a lofty nonwoven reinforcing material disposed between the top facing material layer and the bottom facing material layer the lofty nonwoven material being a through-air bonded carded web (TABCW) material having a basis weight of between 15 gsm and about 60 gsm and made of polyolefin fibers,
      absorbent material comprising superabsorbent material forming a plurality of spaced superabsorbent material lanes disposed between the top facing material layer and the bottom facing material layer and within the reinforcing material, wherein a first side portion of the absorbent body and a second side portion of the absorbent body are folded onto a central portion of the absorbent body forming a folded absorbent body with a first folded portion and a second folded portion with a channel region disposed between the first folded portion and the second folded portion and wherein there is no overlap between superabsorbent lanes in the first folded portion or the second folded portion, and wherein the superabsorbent material lanes spaced from apart by a of distance between 5 mm and 15 mm and a combined width of the superabsorbent material lanes comprises between 40% and 60% of an overall width of the folded absorbent body; and an acquisition material disposed between the absorbent body and the bodyside liner, wherein the acquisition material spans across the channel region and is bonded into the channel.

15. The absorbent garment of claim 14, wherein the acquisition material is bonded to the top facing material layer in the channel region.

16. The absorbent garment of claim 14, wherein the plurality of spaced superabsorbent material lanes on the first side of the reinforcing material laterally overlap with the plurality of spaced superabsorbent material lanes on the second side of the reinforcing material.

17. The absorbent garment of claim 14, wherein regions disposed between the plurality of spaced superabsorbent material lanes are substantially devoid of superabsorbent material.

18. A method of forming an absorbent garment, the method comprising:

moving a first facing material in a machine direction;

moving a reinforcing material in the machine direction, the reinforcing material having a first side and a second side, the reinforcing material being a through-air bonded carded web (TABCW) material having a basis weight of between 15 gsm and about 60 gsm and made of polyolefin fibers;

applying superabsorbent material to the first side of the reinforcing material, the first side of the reinforcing material facing up in a vertical direction, the superabsorbent material being applied in a first series of spaced apart lanes;

reversing an orientation of the reinforcing material so that the first side of the reinforcing material faces down in the vertical direction;

applying the first side of the reinforcing material to the first facing material;

applying superabsorbent material to the second side of the reinforcing material, the superabsorbent material being applied in a second series of spaced apart lanes, wherein the first series of spaced apart lanes and the second series of spaced apart lanes overlap to form regions within the reinforcing material containing superabsorbent material and regions in the reinforcing material devoid of superabsorbent material;

moving a second facing material in the machine direction;

applying the second facing material to the second side of the reinforcing material to form an absorbent laminate comprising the first facing material, the reinforcing material, and the second facing material;

folding a first side portion and a second side portion of the absorbent laminate onto a central portion of the absorbent laminate, the first side portion and the second side portion folded onto the central portion to form a channel region in the folded absorbent laminate, wherein there is no overlap between regions containing superabsorbent material in the first side portion and the central portion and no overlap between regions containing superabsorbent material in the second side portion and the central portion;

moving an acquisition material in the machine direction;

coupling the acquisition material to the folded absorbent laminate such that the acquisition material spans across the channel region;

coupling the folded absorbent laminate and the acquisition material between a bodyside liner material and an outer cover material to form an absorbent garment.

19. The method of claim 18, further comprising bonding the absorbent laminate with heat, pressure, and/or ultrasonic energy to form end edges of the absorbent laminate.

\* \* \* \* \*